US011491202B2

(12) United States Patent
Subramoni et al.

(10) Patent No.: US 11,491,202 B2
(45) Date of Patent: Nov. 8, 2022

(54) HERBAL COMPOSITION

(71) Applicants: KERALA AYURVEDA LIMITED (INDIA), Kerala (IN); KATRA PHYTOCHEM (INDIA) PRIVATE LIMITED, Bangalore (IN)

(72) Inventors: Patanjali Subramoni, Bangalore (IN); Sundaram Chandrasekharan, Bangalore (IN); Jayashree Madhavan, Bangalore (IN); Anilkumar K, Kerala (IN); Sarala Samuel, Kerala (IN); Bishwajit Nag, Union City, CA (US); Ramesh Vangal, Singapore (SG); Nitish Nag, Union City, CA (US); Jayarajan Kodikannath, Fremont, CA (US)

(73) Assignees: KERALA AYURVEDA LIMITED (INDIA), Kerala (IN); KATRA PHYTOCHEM (INDIA) PRIVATE LIMITED, Bangalore (IN)

( * ) Notice: Subject to any disclaimer, the term of this patent is extended or adjusted under 35 U.S.C. 154(b) by 0 days.

(21) Appl. No.: 16/494,609

(22) PCT Filed: Mar. 18, 2018

(86) PCT No.: PCT/IB2018/051790
§ 371 (c)(1),
(2) Date: Sep. 16, 2019

(87) PCT Pub. No.: WO2018/167735
PCT Pub. Date: Sep. 20, 2018

(65) Prior Publication Data
US 2020/0085904 A1    Mar. 19, 2020

Related U.S. Application Data

(60) Provisional application No. 62/473,126, filed on Mar. 17, 2017.

(51) Int. Cl.
| | |
|---|---|
| *A61K 36/00* | (2006.01) |
| *A61K 36/9066* | (2006.01) |
| *A61K 9/00* | (2006.01) |
| *A61K 36/185* | (2006.01) |
| *A61K 36/28* | (2006.01) |
| *A61K 36/48* | (2006.01) |
| *A61K 36/59* | (2006.01) |
| *A61K 36/61* | (2006.01) |
| *A61K 36/74* | (2006.01) |

(52) U.S. Cl.
CPC ........ *A61K 36/9066* (2013.01); *A61K 9/0095* (2013.01); *A61K 36/185* (2013.01); *A61K 36/28* (2013.01); *A61K 36/48* (2013.01); *A61K 36/59* (2013.01); *A61K 36/61* (2013.01); *A61K 36/74* (2013.01); *A61K 2236/331* (2013.01); *A61K 2236/333* (2013.01)

(58) Field of Classification Search
None
See application file for complete search history.

(56) References Cited

U.S. PATENT DOCUMENTS

| 2003/0086987 A1* | 5/2003 | Shiao ................ A61K 36/484 424/746 |
| 2010/0173022 A1* | 7/2010 | Ramautarsing .......... A61P 3/10 424/725 |
| 2012/0035130 A1* | 2/2012 | Peter ...................... A61Q 19/04 514/58 |
| 2014/0147394 A1* | 5/2014 | Chaudhary ............ A61K 36/24 424/43 |

OTHER PUBLICATIONS

PCT International Search Report and Written Opinion for PCT/IB2018/051790, dated Jun. 7, 2018, 9 pages.
Selvaraj et al., "Evaluation of wound healing and antimicrobial potentials of Ixora coccinea root extract", Asian Pacific Journal of Tropical Medicine, Dec. 20, 2011, pp. 959-963.

* cited by examiner

*Primary Examiner* — Russell G Fiebig
(74) *Attorney, Agent, or Firm* — Maschoff Brennan

(57) ABSTRACT

The present invention generally relates to an herbal composition effective in management of disorders related to metabolic syndrome. More particularly, the invention relates to an herbal composition effective in the management of disorders related to metabolic syndrome such as Type 2 diabetes mellitus, obesity and lipid profile management and a process for the preparation of such an herbal composition. The invention further relates to the use of the herbal composition in preparation of food supplements, pharmaceuticals and nutraceuticals for the management of disorders related to metabolic syndrome. The herbal composition effective in management of metabolic syndrome related disorders comprises of herbs selected from *Curcuma longa, Emblica officinalis, Vernonia anthelmintica, Tinospora cordifolia, Trigonella foenum-graecum, Ixora coccinea* and *Syzygium cumini*. Also provided is the use of herbal composition for the treatment of disorders related to metabolic syndrome. Also provided is a method of treating disorders related to metabolic syndrome comprising administering to a subject in need thereof a therapeutically effective amount of the herbal composition of the present invention.

16 Claims, 7 Drawing Sheets

FIG. 10(a)
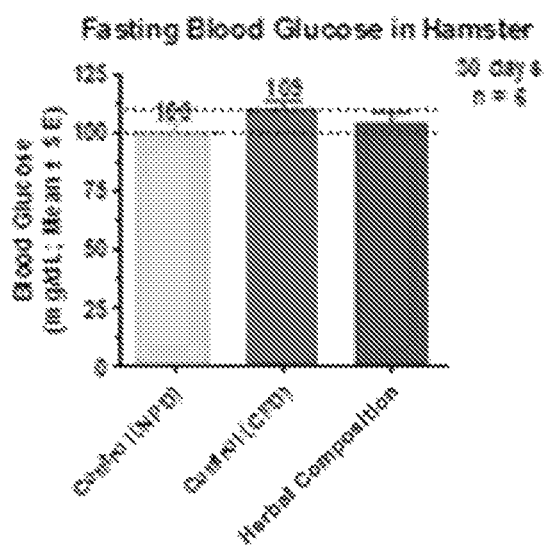
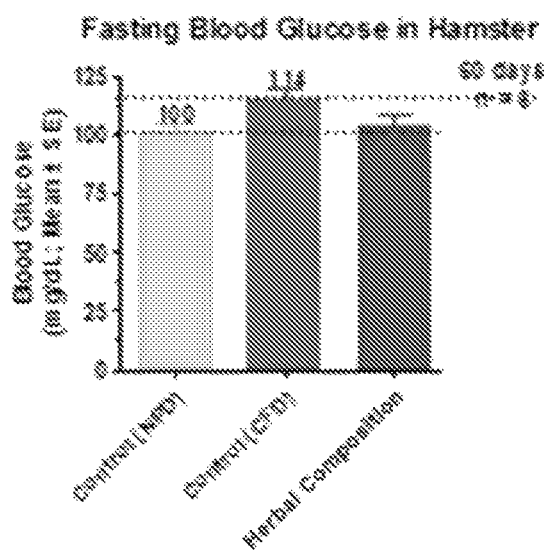
FIG. 10(b)

HERBAL COMPOSITION

CROSS-REFERENCE TO RELATED APPLICATIONS

This Non-Provisional Patent Application is a national stage entry under 35 U.S.C. § 371 of, and claims the benefit of priority to, PCT International Patent Application No. PCT/IB2018/051790, filed on Mar. 18, 2018, which claims priority to U.S. Provisional Application No. 62/473,126, filed on Mar. 17, 2017, the contents of each of which are incorporated by reference herein, in their entireties, including at least those portions concerning herbal compositions and/or metabolism management.

FIELD OF INVENTION

The present invention relates to an herbal composition and in particular to an herbal composition for management of disorders related to metabolic syndrome such as Type 2 diabetes, obesity and lipid profile management and a process for the preparation of such an herbal composition. The invention further relates to the use of the herbal composition in preparation of food supplements, pharmaceuticals and nutraceuticals for management of disorders related to metabolic syndrome. Also provided is the use of herbal composition for the treatment of disorders related to metabolic syndrome. Also provided is a method of treating disorders related to metabolic syndrome comprising administering to a subject in need thereof a therapeutically effective amount of the herbal composition of the present invention.

BACKGROUND OF INVENTION

Metabolic diseases are disorders that disrupt normal metabolism, a process that converts food to energy on a cellular level. They affect the ability of cells to perform critical biochemical processing and transporting proteins, carbohydrates and lipids contained in the foods we consume. A combination of factors, which increase the risk of heart diseases such as stroke, hypertension, hyperlipidemia, hyperglycemia etc., are termed Metabolic Disorder Syndrome.

An increasingly common metabolic disorder of carbohydrate and lipid metabolism is the Type 2 Diabetes mellitus (T2DM), characterized by high blood glucose levels caused due to destruction of islet cells in the pancreas. The two important characteristics of this disease are insulin resistance and dysfunction of pancreatic beta cells. Insulin, produced by the pancreas, is a hormone that facilitates the uptake of glucose in the body and is therefore crucial to glucose metabolism. Insulin resistance (IR) results due to the failure of peripheral tissues such as liver, muscle and adipose to respond to physiological doses of insulin. Also the dysfunction of pancreatic beta cells to properly secrete insulin in response to elevated serum glucose levels is triggered by insulin resistivity. The dual factors of IR and pancreatic beta cells are key to normal glucose metabolism and are tightly linked with behavioral factors such as dietary habits and physical activity (Huijie Wang et al., 2007). It is observed that a large number of subjects suffering from IR are obese. Obesity is considered to increase the risk of IR. Both obesity and IR are inter-related, often termed as conjoined twins. It is roughly estimated that 60-90% of T2DM cases are related to obesity; hence addressing obesity-diabetes connection is vital to treating T2DM. Unfortunately most modern treatment to diabetes contributes to weight gain (James W Anderson et al., 2003).

The first line of treatment of metabolic syndrome involves changes in lifestyle. A healthy lifestyle is considered essential to manage or treat metabolic syndromes. Physical activity such as exercise, yoga, meditation etc., changing to a healthy and balanced diet, losing weight, etc. help to reduce the risk of developing metabolic syndrome related disorders. Control of body weight and reduction of sugars thus play an important role in the treatment of metabolic disorder and in the prevention of Type 2 diabetes mellitus and coronary heart disease.

Oral medications are used when the serum glucose levels are not adequately lowered by the initial life style modifications. The current drugs in the management of diabetes include biguanides (metformin), sulfonyl urea, glitazones, and alpha glucose inhibitors. These drugs, though potent and active, are associated with a series of side effects such as hypoglycemia, coronary heart diseases, nausea, vomiting, dizziness, water retention, weight gain and other adverse effects such as liver disorders, lactic acidosis and diarrhea. Metformin has been reported to cause gastrointestinal side effects, lactic acidosis, dizziness, weakness, etc. Sulphonylurea is a potential teratogen, and its side effects include renal and hepatic diseases. The side effects of Thiazolidinones include water retention, increased risk of coronary heart diseases, etc. The prolonged usage of such drugs has often resulted in the drug becoming ineffective over time resulting in increased dosage and finally leading to the necessity of switching over to Insulin therapy.

Modern therapeutic drugs are not only toxic but also expensive. In this context, it is the need of the present healthcare system to look for an alternative efficient means to tackle the rising cost of medicine and to deliver safe, effective therapeutic solutions. The constant endeavor is to search for the ideal medication that delivers targeted benefits in terms of therapeutic activity, efficacy and more importantly safety as in minimal or absence of undesired effects. This dictates our endless search into natural products and turning to plant based sources for therapeutically active compositions.

Research over the last few decades have come up with several plant extracts that have demonstrable pharmacological activity and growing body of evidence suggests that nature-based products must be the future in drug discovery. It is but a consensus that the ancient medical sciences such as Ayurveda looked to nature to provide safe, effective solutions to address the healthcare needs.

As per ancient literature in Ayurveda, a large number of medicinal plants, either singly or in combinations, have been reported to have anti-diabetic activity. Medicinal plants, namely, *Gymnema sylvestre, Syzigium cumini, Curcuma longa, Emblica officinalis, Cinammomum zeylanicum, Trigonella foenum graecum, Salacia reticulata, Momordica charantia, Tinospora cordifolia, Pterocarpus marsupium, Aegle marmelos, Ixora coccinea* among many others are well known herbs that are widely researched and reported in scientific journals for their powerful anti-diabetic activities. Besides, these are well known for their excellent safety profiles when consumed on a long-term basis (Clifford Bailey et al., 1989). Some of these herbs are proven to provide symptomatic relief and assist in the prevention of secondary complications of the disease. Some herbs help in the regeneration of beta cells and in overcoming insulin resistance. In addition to maintaining normal blood glucose level, certain herbs possess antioxidant activity and lipid lowering action.

The management of Type 2 diabetes mellitus is achieved by using a combination of herbs/or their selective extracts that not only balances serum sugar levels but also restores liver glycogen. In modern medicine, there is no drug that is reported to produce both these actions. The World Health Organization expert committee on diabetes has listed in one of its recommendation that traditional methods of treatment of diabetes should be investigated intensively.

Ayurvedic herbal compositions traditionally being used pose certain limitations such as archaic and/or unfamiliar dosage forms, lack of standardized processes, lack of scientific validation, poor understanding of the mechanism of action, inconsistency in quality and poor shelf-life. Traditionally, the Ayurvedic compositions are administered either as 'kwath' or 'chumas'. Kwath is a term used for the herbal composition given as a water decoction while the term 'chuma' is used for the herbal composition given as a powdered herb/herb blend. The method of preparation of such a 'kwath' and 'chuma' traditionally known, are not definitive, have poor reproducibility and lesser shelf life. For example, the 'kwath', a water decoction of herbs, is traditionally known to be prepared by boiling the herbs in water and is to be consumed fresh. If these have to be stored and consumed over time, preservatives are usually added to increase the shelf life. These preservatives being synthetic chemicals might be harmful on prolonged usage. Besides, such preparations are not standardized in terms of active groups of chemical constituents of the herbal compositions. This leads to improper dose levels.

Therefore, though the herbal compositions are considered a safe alternative for the treatment of metabolic syndrome related disorders such as Type 2 diabetes mellitus, obesity and lipid management, there exists a need for an effective and standardized method for the development of herbal compositions for management of these metabolic syndrome related disorders.

The object of the present invention, therefore, is to provide a novel herbal composition effective in management of metabolic syndrome disorders including Type 2 diabetes mellitus. A further objective of the present invention is to provide a standardized process for the preparation of such a herbal composition leading to a standardized product with specifications that could indicate a batch to batch consistency in terms of certain specific active ingredient composition that are unique to the herbal blends and are believed to contribute to the efficacy of the formulations so prepared and developed. Examples of such actives include curcuminoids, tannins, total organic acids, total poly-phenols etc.

SUMMARY OF INVENTION

The present invention generally relates to an herbal composition effective in the management of disorders related to metabolic syndrome. More particularly, the invention relates to an herbal composition effective in the management of disorders related to metabolic syndrome such as Type 2 diabetes mellitus, obesity and lipid management and the process of preparation of such an herbal composition. The invention further relates to the use of the herbal composition in preparation of food supplements, pharmaceuticals and nutraceuticals for management of disorders related to metabolic syndrome. Also provided is the use of herbal composition for the treatment of disorders related to metabolic syndrome. Also provided is a method of treating disorders related to metabolic syndrome comprising administering to a subject in need thereof a therapeutically effective amount of the herbal composition of the present invention.

According to an aspect of the invention there is provided a herbal composition comprising
a) a first herb blend extract; and
b) a second herb blend extract;
wherein the first herb blend extract is obtained from a first herb blend wherein the first herb blend comprises of at least four herbs selected from *Curcuma longa, Emblica officinalis, Vernonia anthelmintica, Tinospora cordifolia, Trigonella foenum-graecum, Ixora coccinea, Syzygium cumini* or a combination thereof and the second herb blend extract is obtained from a second herb blend wherein the second herb blend comprises of herbs *Curcuma longa* and *Emblica officinalis*; and wherein the first herb blend extract and second herb blend extract are in a ratio of 1:1.

According to an embodiment of the invention there is provided an herbal composition comprising of the herbs selected from *Curcuma longa, Emblica officinalis, Vernonia anthelmintica, Tinospora cordifolia, Trigonella foenum-graecum, Ixora coccinea* and *Syzygium cumini* or a combination thereof wherein the said herbs are present in equal amounts.

According to an embodiment of the invention the first herb blend extract is obtained from a first herb blend wherein the first herb blend optionally comprises of herbs selected from *Curcuma longa, Emblica officinalis, Vernonia anthelmintica, Tinospora cordifolia, Trigonella foenum-graecum* and *Ixora coccinea* or a combination thereof wherein the said herbs are present in equal amounts.

According to an embodiment of the invention the first herb blend extract is obtained from a first herb blend wherein the first herb blend optionally comprises of herbs selected from *Curcuma longa, Emblica officinalis, Vernonia anthelmintica, Tinospora cordifolia* and *Trigonella foenum-graecum* or a combination thereof wherein the said herbs are present in equal amounts.

According to an embodiment of the invention the first herb blend extract is obtained from a first herb blend wherein the first herb blend optionally comprises of herbs selected from *Curcuma longa, Emblica officinalis, Vernonia anthelmintica* and *Tinospora cordifolia* or a combination thereof wherein the said herbs are present in equal amounts.

According to an embodiment of the invention the second herb blend extract is obtained from a second herb blend wherein the second herb blend comprises of herbs *Curcuma longa* and *Emblica officinalis* wherein said herbs are present in a ratio of 1:1 to 1:3.

According to an embodiment of the invention there is provided an Herbal composition comprising a first herb blend extract and a second herb blend extract in a ratio of 1:1.

According to yet another embodiment of the invention the herbal composition may optionally comprise of a single herb extract obtained from a single herb blend comprising of the herbs selected from *Tinospora cordifolia, Trigonella foenum-graecum, Ixora coccinea* and *Syzygium cumini* wherein said herbs are present in equal amounts.

According to yet another embodiment of the invention the herbal composition may be formulated to prepare suitable dosage forms selected from a group comprising powder, paste, granule, capsule, tablet, liquid, lozenges, emulsion, suspension, syrups, elixirs, oral drops, jellies, phytoceuticals, food supplements and nutraceuticals.

According to yet another embodiment of the invention the herbal composition also comprises pharmaceutically acceptable excipients wherein the excipients are selected from a group comprising additives, gums, sweeteners, coatings, binders, disintegrants, lubricants, disintegration agents, suspending agents, granulating agents, solvents, colorants, glidants, anti-adherents, anti-static agents, surfactants, plasticizers, emulsifying agents, flavoring agents, viscosity enhancers and antioxidants to provide a pharmaceutical composition.

According to yet another embodiment of the invention the herbal composition may be used as a food supplement that may be added to various food products such as beverages such as tea, infusions, drinks, water and wheat flour, soups, cookies, biscuits, dairy foods and other processed foods.

According to yet another embodiment of the invention the herbal composition exhibits a synergistic effect in the management of metabolic syndrome related disorders.

According to yet another embodiment of the invention the herbal composition is effective in management of disorders related to metabolic syndrome such as Type 2 diabetes mellitus by controlling the blood glucose and is also effective in managing the lipid profile of an individual.

According to yet another embodiment of the invention the herbal composition of the present invention either arrests body weight gain or prevents body weight gain on a continued therapy basis.

According to yet another embodiment of the invention the herbal composition is free of side effects.

According to yet another embodiment of the invention, the present invention also provides a process of preparation of the herbal composition effective in management of metabolic disorders including Type 2 Diabetes Mellitus, obesity and lipid management. The process of preparation of the herbal composition comprises the following steps:
  a) selection of herbs and specific plant parts of raw herbs to be used;
  b) preparing a first herb blend by determining quantities of the selected herbs for the first herb blend;
  c) preparing a second herb blend by determining the quantities of the selected herbs for the second herb blend;
  d) subjecting the first herb blend to an extraction process using suitable solvents under specific time-temperature combination to obtain a first herb extract;
  e) subjecting the second herb blend to an extraction process using suitable solvents under specific time-temperature combination to obtain a second herb extract;
  f) mixing the first herb extract and the second herb extract obtained in step d) and step e) in a predetermined ratio to obtain an Extract mix;
  g) the Extract mix of Step f) is subjected to further processing such as concentration and/or drying to obtain the herbal composition;
  wherein the first herb blend comprises of at least four herbs selected from *Curcuma longa, Emblica officinalis, Vernonia anthelmintica, Tinospora cordifolia, Trigonella foenum-graecum, Ixora coccinea, Syzygium cumini* or a combination thereof and the second herb blend comprises of *Curcuma longa* and *Emblica officinalis*; and wherein the first herb blend extract and second herb blend extract are in a ratio of 1:1.

According to another embodiment of the invention specific plant parts of the raw herbs may be used such as dried rhizome of *Curcuma longa*, stem of *Tinospora cordifolia*, dried pericarp of *Emblica officinalis*, root of *Ixora coccinea*, bark of *Syzygium cumini*, seeds of *Trigonella foenum-graecum* and fruits of *Vernonia anthelmintica*.

According to an embodiment of the invention the first herb blend may comprise of herbs *Curcuma longa, Emblica officinalis, Vernonia anthelmintica, Tinospora cordifolia, Trigonella foenum-graecum, Ixora coccinea* and *Syzygium cumini* wherein the said herbs are present in equal amounts.

According to an embodiment of the invention the first herb blend may optionally comprise of herbs *Curcuma longa, Emblica officinalis, Vernonia anthelmintica, Tinospora cordifolia, Trigonella foenum-graecum* and *Ixora coccinea* wherein the said herbs are present in equal amounts.

According to an embodiment of the invention the first herb blend may optionally comprise of herbs *Curcuma longa, Emblica officinalis, Vernonia anthelmintica, Tinospora cordifolia* and *Trigonella foenum-graecum* wherein the said herbs are present in equal amounts.

According to an embodiment of the invention the first herb blend may optionally comprise of herbs *Curcuma longa, Emblica officinalis, Vernonia anthelmintica* and *Tinospora cordifolia* wherein the said herbs are present in equal amounts.

According to yet another embodiment of the invention the second herb blend comprises of herbs *Curcuma longa* and *Emblica officinalis* wherein said herbs are present in a ratio of 1:1 to 1:3.

According to another embodiment of the invention the extraction process may be selected from aqueous extraction or hydro-alcohol extraction to obtain a first herb extract and a second herb extract.

According to yet another embodiment of the invention in the hydro-alcohol extraction process a mixture of water and alcohol is taken in a predetermined ratio.

According to yet another embodiment of the invention the first herb extract and the second herb extract are mixed in a predetermined ratio to obtain an Extract Mix, which is further processed such as concentrated to obtain the herbal composition in the form of a paste to be used in preparation of food products such as beverages.

According to yet another embodiment of the invention the first herb extract and the second herb extract are mixed in a predetermined ratio to obtain an Extract Mix, which is further processed such as concentrated and dried to derive the herbal composition.

According to yet another embodiment of the invention the first herb extract and the second herb extract are mixed in a ratio of 1:1 to obtain an Extract Mix.

According to yet another embodiment of the invention the process of preparation of the herbal composition may optionally comprise of selecting a single herb blend comprising of herbs *Tinospora cordifolia, Trigonella foenum-graecum, Ixora coccinea* and *Syzygium cumini* wherein the said herbs are present in equal amounts. The selected herbs are blended in equal amounts and subjected to an extraction process wherein the extraction process may be selected from aqueous extraction or hydro-alcohol extraction to obtain a herb extract. The herb extract is further processed such as concentrated to obtain the herbal composition in the form of a paste to be used in preparation of food products such as beverages. The herb extract may optionally be further concentrated and dried to derive the herbal composition in powder form.

BRIEF DESCRIPTION OF DRAWINGS

The invention can be described in the terms of the following figures where—

FIG. 10(a) shows the comparison of results of Fasting Blood Glucose at 30 days in Hamsters when fed with the herbal composition, cholesterol fed diet and Control Diet for a period of 30 days.

FIG. 10(b) shows the comparison of results of Fasting Blood Glucose at 60 days in Hamsters when fed with the herbal composition, cholesterol fed diet and Control Diet for a period of 60 days.

FIG. 12 (a) shows the comparison of Total cholesterol at 90 days in Apo E(-/-) mice when fed with the herbal composition, cholesterol fed diet and Control Diet for a period of 90 days.

DETAILED DESCRIPTION OF INVENTION

Figure 1:
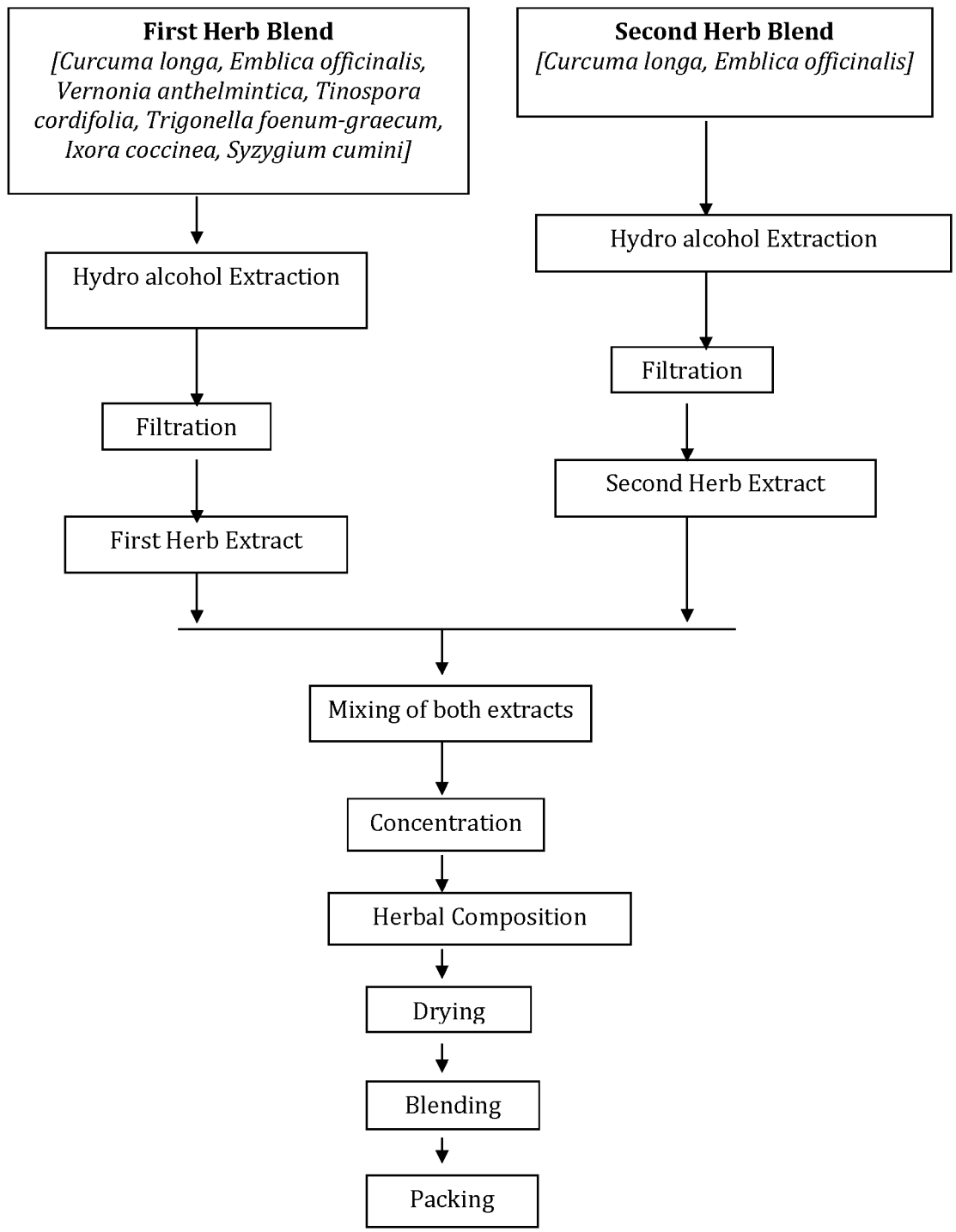
FIG. 1 shows the process flow chart followed for the preparation of the Herbal Composition.

Discussed below are some representative embodiments of the present invention. The invention in its broader aspects is not limited to the specific details and representative methods. On the contrary, it is intended to cover alternatives, modifications, and equivalents as may be included within the spirit and scope of the invention as defined by the appended claims. The illustrative examples are described in this section in connection with the embodiments and methods provided. The invention according to its various aspects is particularly pointed out and distinctly claimed in the attached claims read in view of this specification.

All cited references are incorporated herein by reference in their entireties. Citation of any reference is not an admission regarding any determination as to its availability as prior art to the claimed invention.

It is to be noted that, as used in the specification and the appended claims, the singular forms "a," "an," and "the" include plural referents unless the context clearly dictates otherwise. Thus, for example, reference to a composition containing "a compound" includes a mixture of two or more compounds. It should also be noted that the term "or" is generally employed in its sense including "and/or" unless the content clearly dictates otherwise.

The expression of various quantities in terms of "%" means the percentage by weight of the total solution or composition unless otherwise specified.

Technical and scientific terms used herein have the meaning commonly understood by one of skill in the art to which the present invention pertains, unless otherwise defined. Reference is made herein to various methodologies and materials known to those of skill in the art.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "extract" refers to the paste resulting from (1) exposing a botanical herb to a solvent, (2) separating the solvent from the plant products, and (3) removing the solvent.

As used herein, the term "solvent" refers to a liquid of aqueous or organic nature possessing the necessary characteristics to extract the actives from the herbs.

The present invention, in its product and process aspects, is described in detail as follows.

The present invention provides for an herbal composition effective in the management of disorders related to metabolic syndrome. More particularly, the invention relates to an herbal composition effective in the management of disorders related to metabolic syndrome such as Type 2 diabetes mellitus, obesity and lipid management and the process of preparation of such an herbal composition. The invention further relates to the use of the herbal composition in preparation of food supplements, pharmaceuticals and nutraceuticals for management of disorders related to metabolic syndrome. Also provided is a method of treating disorders related to metabolic syndrome comprising administering to a subject in need thereof a therapeutically effective amount of the herbal composition of the present invention. Also provided is the use of herbal composition for the treatment of disorders related to metabolic syndrome.

According to an embodiment of the invention there is provided an herbal composition comprising of at least four herbs selected from *Curcuma longa, Emblica officinalis, Vernonia anthelmintica, Tinospora cordifolia, Trigonella foenum-graecum, Ixora coccinea* and *Syzygium cumini* or a combination thereof.

Herbs:

*Curcuma longa*

*Curcuma longa*, commonly known as Turmeric, belongs to the Zingiberaceae family. The use of its rhizome is well known for its medicinal properties. The rhizome has been widely used in several Ayurvedic preparations. Curcumin is one of the chief active ingredients present in *Curcuma longa*. Curcumin is the best-researched active constituent and comprises 0.3-5.4 percent of raw turmeric (Leung A, 1980). Curcumin is known for its diverse pharmacological activities such as pain and inflammation, arthritis (Funk, J. L. et al., 2009), Wound healing (Phan, T. T. et al., 2001), Cardiovascular diseases, Diabetes mellitus, Multiple sclerosis, Cataract, Alzheimer disease, Gall stones, Inflammatory Bowel Syndrome, antioxidant, antibacterial etc. The herb is native to Southeast Asia and is widely distributed in India and Pakistan.

*Emblica officinalis*

*Emblica officinalis*, also known as Amla or Indian gooseberry is a deciduous tree that belongs to the Phyllanthaceae family. The use of its fruit rinds for its medicinal properties in Ayurvedic compositions is well known. In traditional Indian medicine, dried, fresh fruits rinds are generally used. It is used as a Rasayana drug (rejuvenative) to promote longevity, and traditionally to enhance digestion, treat constipation, reduce fever, purify the blood, reduce cough, alleviate asthma, strengthen the heart, benefit the eyes, stimulate hair growth, enliven the body, and enhance intellect. Various research studies have shown that Amla fruit possesses antioxidant (Bhattacharya, A. et al, 1999), hepatoprotective (jeena, K. J., et al., 1999), hypocholesterolemic (Mishra, M. et al., 1981) and anti-inflammatory activities (Asmawi, M. Z., et al., 1993). It is widely found in India.

*Vernonia anthelmintica*

*Vernonia anthelmintica*, also known as Purple fleabane or Kaalijeeri, belongs to the family Asteraceae. The use of the fruits in herbal formulations is well known. The fruits are bitter, acrid, thermogenic, anthelmintic, astringent, anti-inflammatory, anodyne, expectorant, depurative, demulcent, purgative, diuretic, stomachic, febrifuge, galactogogue and tonic. They are useful in inflammations, hiccough, cough, asthma, leprosy, skin diseases, pruritus, leucoderma, dyspepsia, colic, strangury, fever, opthalmopathy, vitiated conditions of vata and are very specific for roundworm and threadworm. *V. anthelmintica* is used to control Diabetes (Rao, U. M. et al., 2010). It is widely found in India.

*Tinospora cordifolia*

*Tinospora cordifolia*, commonly known as Guduchi or Giloya, is an herbaceous vine that belongs to the family Menispermaceae. The plant is used in Ayurvedic "Rasayanas" to improve the immune system and body resistance against infections. The extracts of the various parts of the plant including leaves and stem are used in various traditional medicinal formulations. The stem is bitter, astringent, thermogenic, anodyne, anthelmintic, alterant, antiperiodic, antispasmodic, anti-inflammatory, antipyretic, anti-emetic, digestive, carminative, appetizer, stomachic, constipating, cardiotonic, depurative, haematinic, expectorant, aphrodisiac, rejuvenating, galacto-purifier and tonic. *T. cordifolia* is widely used in Ayurvedic medicine for treating diabetes milletus (Stanely, M. et al., 2001; Prince, P. S. and Menon. V. P., 1999; Matthew, S. and Kuttan, G. 1999). It is useful in vitiated conditions of vata, burning sensation, hyperdipsia, helminthiasis, dyspepsia, flatulence, stomachalgia, intermittent fevers, chronic fevers, inflammations, gout, vomiting, cardiac debility, skin diseases, leprosy, erysipelas, anaemia, cough, asthma, general debility, jaundice, seminal weakness, uropathy and splenopathy. It is widely found in India, Myanmar and Srilanka.

*Trigonella foenum-graecum*

*Trigonella foenum-graecum*, commonly known as Fenugreek, belongs to the family Fabaceae. The leaves and seeds of the plant are known to be of high medicinal value. The leaves are refrigerant and aperients and are given internally for vitiated conditions of pitta. A poultice of the leaves is applied for swellings and burns. Fenugreek seeds are a good source of dietary fiber, which form the most important constituent of this herb. Rich in soluble and insoluble fibers, Fenugreek plays an important role in controlling metabolic syndrome. Fenugreek seeds are bitter, mucilaginous, aromatic, carminative, tonic, thermogenic, galactogogue, astringent, emollient and an aphrodisiac. They are useful in treating fever, vomiting, anorexia, cough, bronchitis and colonitis. Powdered seeds find application in veterinary medicine. An aqueous extract of the seed possesses antibacterial property. In humans, fenugreek seeds exert hypoglycemic effects by stimulating glucose-dependent insulin secretion from pancreatic beta cells (Ajabnoor, M. A. and Tilmisany, A. K. 1988), as well as by inhibiting the activities of alpha-amylase and sucrose (Amin, R. et al., 1987), two intestinal enzymes involved in carbohydrate metabolism. It is found widely distributed across the world including India, Bangladesh, and Nepal.

*Ixora coccinea*

*Ixora coccinea* or Jungle geranium is a flowering plant, which belongs to the family Rubiaceae. The roots, leaves and flowers of the plant have medicinal properties and are used in various traditional medicinal formulations. The roots are astringent, acrid, febrifuge, sedative, stomachic and antiseptic in nature. It is useful in hiccough, fever, gonorrhea, anorexia, diarrhea, dysentery, cephalalgia, sores, chronic ulcers and skin diseases. The leaves are useful in diarrhea. The leaves exhibit a cardioprotective effect due to its antioxidant properties (Firoz, N et al., 2012). The flowers are useful as an astringent, bitter, carminative, digestive and in constipation. The flowers are antidiarrheal (Yasmeen, M. et al., 2010). They are useful in dysentery, dysmenorrhoea, leucorrhoea, haemoptysis, catarrhal bronchitis, ophthalmopathy, sores and ulcers. It is widely found in India and Sri Lanka.

*Syzygium cumini*

*Syzygium cumini*, commonly known as Jamun, is an evergreen tropical tree, which belongs to the family Myrtaceae. The leaves, bark, and fruits including the seeds of the plant are used in various therapeutic formulations. The bark is astringent, acrid, refrigerant, carminative, diuretic, digestive, anthelmintic, febrifuge, constipating, antibacterial and stomachic. It is useful in treating diabetes, leucorrhoea, stomachalgia, fever, gastropathy, strangury and dermatopathy. The leaves are antibacterial and are used for strengthening the teeth and gums. The tender leaves are used to treat vomiting. The fruits and seeds are sweet, acrid, sour, tonic and cooling and are widely used as a valuable anti-diabetic nutrient (Sagrawat, H. et al., 2006). The fruits and seeds are also useful in diarrhea, pharyngitis, splenopathy, urethrorrhea and ringworm. It is native to India, Bangladesh, Nepal and Pakistan.

The present invention provides for an Herbal composition comprising a first herb blend extract and a second herb blend extract in a ratio of 1:1 wherein the first herb blend extract is obtained from a first herb blend wherein the first herb blend comprises of at least four herbs selected from *Curcuma longa, Emblica officinalis, Vernonia anthelmintica, Tinospora cordifolia, Trigonella foenum-graecum, Ixora coccinea, Syzygium cumini* or a combination thereof and the second herb blend extract is obtained from a second herb blend wherein the second herb blend comprises of herbs *Curcuma longa* and *Emblica officinalis*.

According to an embodiment of the invention the first herb blend extract is obtained from a first herb blend wherein the first herb blend comprises of herbs selected from *Curcuma longa, Emblica officinalis, Vernonia anthelmintica, Tinospora cordifolia, Trigonella foenum-graecum, Ixora*

*coccinea, Syzygium cumini* or a combination thereof wherein the said herbs are present in equal amounts.

In an embodiment of the invention the first herb blend extract is obtained from a first herb blend wherein the first herb blend optionally comprises of herbs namely *Curcuma longa, Emblica officinalis, Vernonia anthelmintica, Tinospora cordifolia, Trigonella foenum-graecum* and *Ixora coccinea* or a combination thereof wherein the said herbs are present in equal amounts.

In an embodiment of the invention the first herb blend extract is obtained from a first herb blend wherein the first herb blend optionally comprises of herbs namely *Curcuma longa, Emblica officinalis, Vernonia anthelmintica, Tinospora cordifolia* and *Trigonella foenum-graecum* or a combination thereof wherein the said herbs are present in equal amounts.

In an embodiment of the invention the first herb blend extract is obtained from a first herb blend wherein the first herb blend optionally comprises of herbs namely *Curcuma longa, Emblica officinalis, Vernonia anthelmintica* and *Tinospora cordifolia* or a combination thereof wherein the said herbs are present in equal amounts.

The second herb blend extract is obtained from a second herb blend wherein the second herb blend comprises of *Curcuma longa* and *Emblica officinalis* wherein said herbs are present in a ratio of 1:1 to 1:3.

In an embodiment of the invention the second herb blend comprises of herbs *Curcuma longa* and *Emblica officinalis* in a ratio of 1:1.

In an embodiment of the invention the second herb blend comprises of herbs *Curcuma longa* and *Emblica officinalis* in a ratio of 1:2.

In an embodiment of the invention the second herb blend comprises of herbs *Curcuma longa* and *Emblica officinalis* in a ratio of 1:3.

According to an embodiment of the invention the herbal composition may optionally comprise of a single herb extract obtained from a single herb blend comprising of the herbs *Tinospora cordifolia, Trigonella foenum-graecum, Ixora coccinea* and *Syzygium cumini* wherein said herbs are present in equal amounts.

According to an embodiment of the invention the first herb blend and the second herb blend are subjected to an extraction process using suitable solvents under specific time-temperature combination to obtain a first herb extract and a second herb extract which extracts are mixed in a predetermined ratio to obtain an Extract Mix which is subjected to further processing to obtain the herbal composition of the present invention.

According to an embodiment of the invention the first herb extract and the second herb extract are mixed in a ratio of 1:1, which Extract Mix is then subjected to further processing.

According to an embodiment of the invention the herbal composition may optionally comprise of herbs *Tinospora cordifolia, Trigonella foenum-graecum, Ixora coccinea* and *Syzygium cumini* which are taken in equal quantities to form a herb blend and this herb blend is then subjected to an extraction process using suitable solvents under specific time-temperature combination to obtain an extract which is further processed to derive the herbal composition of the present invention.

In an embodiment of the invention the herbal composition may be formulated to prepare suitable dosage forms selected from a group comprising powder, paste, granule, capsule, tablet, liquid, lozenges, emulsion, suspension, syrups, elixirs, oral drops, jellies, phytoceuticals, food supplements and nutraceuticals.

In an embodiment of the invention the herbal composition may also comprise of pharmaceutically acceptable excipients wherein the excipients are selected from a group comprising additives, gums, sweeteners, coatings, binders, disintegrants, lubricants, disintegration agents, suspending agents, granulating agents, solvents, colorants, glidants, anti-adherents, anti-static agents, surfactants, plasticizers, emulsifying agents, flavoring agents, viscosity enhancers and antioxidants to provide a pharmaceutical composition.

According to another embodiment of the invention the herbal composition may be used as a food supplement that may be added to various food products such as beverages such as tea, infusions, drinks, water, wheat flour, soups, cookies, biscuits, dairy foods and other processed foods.

The herbal composition of the present invention exhibits a synergistic effect in the management of metabolic syndrome related disorders.

The herbal composition of the present invention is effective in management of disorders related to metabolic syndrome such as Type 2 diabetes mellitus by controlling the blood glucose. The herbal composition is also effective in lipid management of an individual.

In vitro glucose uptake study conducted to assess the efficacy of the herbal composition versus the raw herbs shows that the herbal composition exhibits synergistic activity showing higher glucose uptake than the individual herbs when tested at different concentrations.

The pre-clinical studies conducted on the herbal composition of the present invention using various animal models show that the herbal composition of the present invention prevents body weight gain on a continued therapy basis.

The pre-clinical studies conducted on the herbal composition of the present invention using various animal models further show that the herbal composition of the present invention arrests body weight gain.

It can also be inferred from the pre-clinical studies conducted on the herbal composition of the present invention using various animal models that the herbal composition of the present invention decreases serum glucose, fasting blood glucose and oral glucose tolerance test (OGTT).

The pre-clinical studies conducted on the herbal composition of the present invention exhibit a reasonable decrease in serum total triglyceride in 60 days treatment.

The pre-clinical studies conducted on the herbal composition of the present invention exhibit a reasonable reduction in serum total triglyceride and serum cholesterol in 180 days treatment.

In accordance to another embodiment of the invention the herbal composition is free of side effects and the same is established by toxicity study.

According to yet another embodiment of the invention the efficacy of the herbal composition is maintained during storage and the same is established by HPLC fingerprint to result a consistent phytochemical profile.

The present invention also provides the process of preparation of the herbal composition effective in management of metabolic disorders including Type 2 Diabetes Mellitus, obesity and lipid management. The process of preparation of the herbal composition comprises the following steps:
   a) selection of herbs and specific plant parts of raw herbs to be used;
   b) preparing a first herb blend by determining quantities of the selected herbs for the first herb blend;

c) preparing a second herb blend by determining the quantities of the selected herbs for the second herb blend;
d) subjecting the first herb blend to an extraction process using suitable solvents under specific time-temperature combination to obtain a first herb extract;
e) subjecting the second herb blend to an extraction process using suitable solvents under specific time-temperature combination to obtain a second herb extract;
f) mixing the first herb extract and the second herb extract obtained in step d) and step e) in a ratio of 1:1 to obtain an Extract mix;
g) the Extract mix of Step f) is subjected to further processing such as concentration and/or drying to obtain the herbal composition;
wherein the first herb blend comprises of at least four herbs selected from *Curcuma longa, Emblica officinalis, Vernonia anthelmintica, Tinospora cordifolia, Trigonella foenum-graecum, Ixora coccinea, Syzygium cumini* or a combination thereof and the second herb blend comprises of herbs *Curcuma longa* and *Emblica officinalis*.

The first herb blend comprises of herbs selected from the group consisting of *Curcuma longa, Emblica officinalis, Vernonia anthelmintica, Tinospora cordifolia, Trigonella foenum-graecum, Ixora coccinea* and *Syzygium cumini* wherein the said herbs are present in equal amounts.

In an embodiment of the invention the first herb blend comprises of herbs optionally selected from the group consisting of *Curcuma longa, Emblica officinalis, Vernonia anthelmintica, Tinospora cordifolia, Trigonella foenum-graecum* and *Ixora coccinea* wherein the said herbs are present in equal amounts.

In accordance to an embodiment of the invention the first herb blend comprises of herbs optionally selected from the group consisting of *Curcuma longa, Emblica officinalis, Vernonia anthelmintica, Tinospora cordifolia* and *Trigonella foenum-graecum* wherein the said herbs are present in equal amounts.

In accordance to an embodiment of the invention the first herb blend comprises of herbs optionally selected from the group consisting of *Curcuma longa, Emblica officinalis, Vernonia anthelmintica* and *Tinospora cordifolia* wherein the said herbs are present in equal amounts.

In an embodiment of the invention the second herb blend comprises of herbs *Curcuma longa* and *Emblica officinalis* wherein said herbs are present in a ratio of 1:1 to 1:3.

In an embodiment of the invention the second herb blend comprises of herbs *Curcuma longa* and *Emblica officinalis* wherein said herbs are present in a ratio of 1:1.

In an embodiment of the invention the second herb blend comprises of herbs *Curcuma longa* and *Emblica officinalis* wherein said herbs are present in a ratio of 1:2.

In an embodiment of the invention the second herb blend comprises of herbs *Curcuma longa* and *Emblica officinalis* wherein said herbs are present in a ratio of 1:3.

According to another embodiment of the invention specific plant parts of the raw herbs may be used such as dried rhizome of *Curcuma longa*, stem of *Tinospora cordifolia*, dried pericarp of *Emblica officinalis*, root of *Ixora coccinea*, bark of *Syzygium cumini*, seeds of *Trigonella foenum-graecum* and fruits of *Vernonia anthelmintica*.

In an embodiment of the invention the specific plant parts of the herbs in the first herb blend may comprise of dried rhizome of *Curcuma longa*, stem of *Tinospora cordifolia*, dried pericarp of *Emblica officinalis*, root of *Ixora coccinea*, bark of *Syzygium cumini*, seeds of *Trigonella foenum-graecum* and fruits of *Vernonia anthelmintica*. The specific plant parts of the selected herbs may be ground into a coarse powder, which powder is then subjected to the extraction process.

In accordance with another embodiment of the invention the specific plant parts of the second herb blend may comprise of dried rhizome of *Curcuma longa* and dried pericarp of *Emblica officinalis*. The specific plant parts of the selected herbs may be ground into a coarse powder, which powder is then subjected to the extraction process.

In an embodiment of the invention the herbal composition may optionally comprise of herbs *Tinospora cordifolia, Trigonella foenum-graecum, Ixora coccinea* and *Syzygium cumini* which are taken in equal quantities to form a single herb blend. The specific plant parts of the herbs in the said herb blend may comprise of stem of *Tinospora cordifolia*, seeds of *Trigonella foenum-graecum*, root of *Ixora coccinea* and bark of *Syzygium cumini*. The specific plant parts of the selected raw herbs may be ground into a coarse powder, which powder is then subjected to the extraction process.

The extraction process for the herb blends may be selected from aqueous extraction or hydro-alcohol extraction.

According to an embodiment of the invention a hydro-alcohol mixture of solvent is used in the hydro-alcohol extraction process. The hydro-alcohol mixture of solvent for extraction comprises of a mixture of alcohol and water wherein alcohol and water are taken in a predetermined ratio. The alcohol and water may be taken in a ratio ranging from 80:20 to 20:80 to prepare the hydro-alcohol mixture of solvent for the hydro-alcohol extraction process. Preferably, the ratio of alcohol and water may be kept as 50:50 or 70:30 in the hydro-alcohol mixture of solvent for the hydro-alcohol extraction process.

According to another embodiment of the invention the herbs of first herb blend are subjected to aqueous extraction to obtain a first herb extract.

According to another embodiment of the invention the herbs of first herb blend are subjected to hydro-alcohol extraction process to obtain a first herb extract wherein the mixture of alcohol and water used in the hydro-alcohol mixture of solvent is in a ratio of 70:30.

According to another embodiment of the invention the herbs of second herb blend are subjected to aqueous extraction to obtain a second herb extract.

According to another embodiment of the invention the herbs of second herb blend are subjected to hydro-alcohol extraction process to obtain a second herb extract wherein the mixture of alcohol and water used in the hydro-alcohol mixture of solvent for the hydro-alcohol extraction process is in a ratio of 70:30.

According to an embodiment of the invention the alcohol in the hydro-alcohol mixture of solvent for the hydro-alcohol extraction process may be selected from methyl alcohol, ethyl alcohol and iso-propyl alcohol, preferably ethyl alcohol.

In an embodiment of the invention the first herb blend and the second herb blend respectively may be extracted using a suitable solvent at reflux or under circulation at 75° C. for 2 hours. The ratio of raw herbs and solvent used in extraction may be 1:10 to obtain a first herb extract and a second herb extract. The extraction process may further be repeated 2 or 3 times.

According to an embodiment of the invention the first herb extract and the second herb extract thus obtained may be subjected to further processing such as concentration and then blended in predetermined quantities to obtain the herbal composition in the form of a paste. The first and second herb extracts may be blended in equal quantities to derive the herbal composition in the form of a paste.

According to yet another embodiment of the invention the process of preparation of the herbal composition may optionally comprise of selecting a single herb blend comprising of herbs *Tinospora cordifolia, Trigonella foenum-graecum, Ixora coccinea* and *Syzygium cumini* wherein the said herbs are present in equal amounts. The selected herbs are blended in equal amounts and subjected to an extraction process wherein the extraction process may be selected from aqueous extraction or hydro-alcohol extraction to obtain a herb extract. The alcohol and water may be taken in a ratio ranging from 80:20 to 20:80 to prepare the hydro-alcohol mixture of solvent for the hydro-alcohol extraction. Preferably, the ratio of alcohol and water may be kept as 50:50 or 70:30 in the hydro-alcohol mixture of solvent for the hydro-alcohol extraction. The alcohol in the hydro-alcohol mixture of solvent for hydro-alcohol extraction process may be selected from methyl alcohol, ethyl alcohol and iso-propyl alcohol, preferably ethyl alcohol.

In an embodiment of the invention the herb blend optionally comprising of herbs *Tinospora cordifolia, Trigonella foenum-graecum, Ixora coccinea* and *Syzygium cumini* is subjected to the hydro-alcohol extraction process to obtain a herb extract wherein the mixture of alcohol and water used for hydro-alcohol mixture of solvent in the hydro-alcohol extraction process is in a ratio of 70:30. The extraction is carried out at reflux or under circulation at 75° C. for 2 hours. The ratio of raw herbs and solvent used in extraction may be 1:10 to obtain a herb extract. The extraction process may further be repeated 2 or 3 times. The herb extract thus obtained may be further processed such as concentrated to obtain the herbal composition in the form of a paste to be used in preparation of food products such as beverages. Optionally, the herb extract thus obtained may be further processed such as dried to obtain the herbal composition in the form of a powder.

According to an embodiment of the invention the herbal composition obtained in the form of a paste may be used as food supplement that may be added to various food products. The food products may include but are not limited to beverages such as tea, infusions, drinks, water, wheat flour, soups, cookies, biscuits, dairy foods/drinks and other processed foods.

According to yet another embodiment of the invention the first herb extract and the second herb extract thus obtained may be subjected to further processing such as concentration and drying. The drying may be carried out using a Fluid Bed dryer or a Tray drier The dried powder obtained from first and second dried herb extracts may be then blended in predetermined amounts to derive the dried/powdered herbal composition.

According to yet another embodiment of the invention the dried powder obtained from first and second dried herb extracts are blended in equal quantities to derive the dried/powdered herbal composition.

The herbal composition obtained in the form of a dry powder may be used as food supplement that may be added to various food products. The food products may include but are not limited to beverages such as tea, infusions, drinks, water, wheat flour, soups, cookies, biscuits, dairy foods/drinks and other processed foods.

According to an embodiment of the invention the herbal composition obtained in the form of a dry powder may be formulated to prepare suitable dosage forms selected from a group comprising powder, granule, capsule, tablet, liquid, lozenges, emulsion, suspension, syrups, elixirs, oral drops, jellies, phytoceuticals, food supplements and nutraceuticals.

According to yet another embodiment of the invention the herbs used in the preparation of the herbal composition may be used as a raw whole or crushed plant or as extract (standardized extract, quantified extract, other extract, alcoholic/aqueous extract or any combination thereof). Since active compounds can be found in higher concentrations in specific parts of herbs/medicinal plants, but are present to a lesser extent in other parts of the herb/medicinal plant as well, all parts of the herbs/medicinal plants (roots, fruits, seeds, leaves, wood, or whole plants) can be processed.

According to an embodiment of the invention the process of preparation may optionally comprise grinding the specific plant parts of the selected herbs/plants into a coarse powder before the extraction process.

According to an embodiment of the invention the process to obtain the herbal composition comprises pulverizing and sifting the raw herbs of first herb blend. The pulverized herbs of first herb blend are then extracted using a suitable solvent at reflux or under circulation at 75° C. for 2 hours. The extraction process may be repeated 2 or 3 times. The ratio of raw herbs and solvent used in extraction is 1:10. The hydro-alcohol mixture of solvent used for hydro-alcohol extraction process may comprise alcohol and water in a ratio ranging from 80:20 to 20:80, preferably 70:30. The alcohol used in the hydro-alcohol mixture of solvent for hydro-alcohol extraction process may be selected from methyl alcohol, ethyl alcohol and iso-propyl alcohol, preferably ethyl alcohol. The extract is then filtered through a suitable filter medium under gravity pressure to obtain a first Extract Solution. The filter medium may be a 15 micron filter cloth. The herbs of second Herb Blend are separately pulverized and sifted and these herbs of second Herb Blend are extracted using a suitable solvent at reflux or under circulation at 75° C. for 2 hours. The ratio of raw herbs and solvent used in extraction is 1:10. The hydro-alcohol mixture of solvent used for hydro-alcohol extraction process may comprise alcohol and water in a ratio ranging from 80:20 to 20:80, preferably 70:30. The alcohol used in the hydro-alcohol mixture of solvent for hydro-alcohol extraction process may be selected from methyl alcohol, ethyl alcohol and iso-propyl alcohol, preferably ethyl alcohol. The extraction process may be repeated 2 or 3 times. The extract thus obtained is then filtered through a suitable filter medium under gravity pressure to obtain a second Extract Solution. The filter medium may be a 15 micron filter cloth. The first Extract Solution and the second Extract Solution are then mixed and concentrated at a predetermined temperature to a predetermined concentration. The first Extract Solution and the second Extract Solution are mixed to obtain an Extract Mix which is then distilled at a temperature of 60° C.-65° C. and further concentrated at a temperature of 70° C.-75° C. under vacuum at 400 to 550 mmHg pressure to obtain a concentrated Extract Mix. The concentrated Extract mix may be subjected to further processing to convert it into different forms of the Herbal Composition. The product thus obtained is a safe, effective and stable herbal composition with a good shelf life and efficacy.

According to an embodiment of the invention the process to obtain the herbal composition comprises pulverizing and sifting the raw herbs of the herb blend comprising of herbs *Tinospora cordifolia, Trigonella foenum-graecum, Ixora coccinea* and *Syzygium cumini* taken in equal quantities. The pulverized herbs of the herb blend are then extracted using a suitable solvent at reflux or under circulation at 75° C. for 2 hours. The ratio of raw herbs and solvent used in extraction is 1:10. The hydro-alcohol mixture of solvent used for hydro-alcohol extraction process may comprise alcohol and water in a ratio ranging from 80:20 to 20:80, preferably 70:30. The alcohol used in the hydro-alcohol mixture of solvent for hydro-alcohol extraction process may be selected from methyl alcohol, ethyl alcohol and iso-propyl alcohol, preferably ethyl alcohol. The extraction process may further be repeated 2 or 3 times. The extract is then filtered through a suitable filter medium under gravity pressure to obtain an Extract Solution. The filter medium may be a 15 micron filter cloth. The Extract Solution is then concentrated at a predetermined temperature to a predetermined concentration. The Extract Solution is then distilled at a temperature of 60° C.-65° C. and further concentrated at a temperature of 70° C.-75° C. under vacuum at 400 to 550 mmHg pressure to obtain a concentrated extract. The concentrated extract may be subjected to further processing to convert it into different forms of the Herbal Composition. The product thus obtained is a safe, effective and stable herbal composition with a good shelf life and efficacy.

According to another embodiment of the invention, process of preparation of herbal composition may optionally comprise subjecting the herbal composition to further processing to formulate a suitable dosage form.

The shelf life of the herbal composition of the present invention in powder form is at least 3 years.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

In this example, representative herbal composition of present invention is described that is prepared by the process as shown in FIG. 1 and formulated into the herbal composition in dry powder form, wherein the first Herb Blend comprises of herbs *Curcuma longa, Emblica officinalis, Vernonia anthelmintica, Tinospora cordifolia, Trigonella foenum-graecum, Ixora coccinea* and *Syzygium cumini* in equal amounts and the second Herb Blend comprises of herbs *Curcuma longa* and *Emblica officinalis* in a ratio of 1:3. Table 1 shows the ingredients and their amounts in percentage by weight.

TABLE 1

Components used for preparation of Herbal Composition

| Ingredients Name | Ingredients amount (% by wt.) |
|---|---|
| First Herb Blend | |
| *Curcuma longa* | 7.143 |
| *Emblica officinalis* | 7.143 |
| *Vernonia anthelmintica* | 7.143 |
| *Tinospora cordifolia* | 7.143 |
| *Trigonella foenum graecum* | 7.143 |
| *Ixora coccinea* | 7.143 |
| *Syzygium cumini* | 7.143 |
| Second Herb Blend | |
| *Curcuma longa* | 12.50 |
| *Emblica officinalis* | 37.50 |

The extracts obtained from first herb blend and second herb blend are mixed in a ratio of 1:1 and further processed such as dried to obtain a herbal composition in dry powder form. Table 1a shows the Proximate Composition of the dried Herbal Composition as analysed. The actives present in the Herbal Composition were measured using suitable methods such as Total tannins and Total organic acids as Gallic acid were measured by Titration. Total polyphenols by UV-visible spectroscopy and content of Gallic Acid, Ellagic acid and Curcuminoids was measured by HPLC.

TABLE 1a

Composition of the Actives in the Herbal Composition:

| Actives | % |
|---|---|
| Content of Total tannins | 20.29 |
| Content of Total organic acids as Gallic acid | 11.22 |
| Content of Total Polyphenols as Catechin | 20.73 |
| Gallic Acid | 3.90 |
| Ellagic Acid | 0.88 |
| Curcuminoids | 0.98 |

Example 2

In this example, representative herbal composition of present invention is described that is prepared and formulated into the herbal composition in dry powder form, wherein the first Herb Blend comprises of herbs *Curcuma longa, Emblica officinalis, Vernonia anthelmintica, Tinospora cordifolia, Trigonella foenum-graecum, Ixora coccinea* and *Syzygium cumini* in equal amounts and the second Herb Blend comprises of herbs *Curcuma longa* and *Emblica officinalis* in a ratio of 1:1. Table 2 shows the ingredients and their amounts in percentage by weight. Table 2a shows the Proximate Composition of the dried Herbal Composition as analysed. The actives present in the Herbal Composition were measured using suitable methods such as Total tannins and Total organic acids as Gallic acid were measured by Titration, Total polyphenols by UV-visible spectroscopy and content of Gallic Acid, Ellagic acid and Curcuminoids was measured by HPLC.

TABLE 2

Components used for preparation of Herbal Composition

| Ingredients Name | Ingredients amount (% by wt.) |
|---|---|
| First Herb Blend | |
| *Curcuma longa* | 7.143 |
| *Emblica officinalis* | 7.143 |
| *Vernonia anthelmintica* | 7.143 |
| *Tinospora cordifolia* | 7.143 |
| *Trigonella foenum graecum* | 7.143 |
| *Ixora coccinea* | 7.143 |
| *Syzygium cumini* | 7.143 |
| Second Herb Blend | |
| *Curcuma longa* | 25 |
| *Emblica officinalis* | 25 |

TABLE 2a

Composition of the Actives in the Herbal Composition:

| Actives | % |
| --- | --- |
| Content of Total tannins | 14.8 |
| Content of Total organic acids as Gallic acid | 8.2 |
| Content of Total Polyphenols as Catechin | 15.5 |
| Gallic Acid | 2.6 |
| Ellagic Acid | 0.6 |
| Curcuminoids | 1.23 |

Example 3

In this example, representative herbal composition of present invention is described that is prepared and formulated into the herbal composition in dry powder form, wherein the first Herb Blend comprises of herbs *Curcuma longa, Emblica officinalis, Vernonia anthelmintica, Tinospora cordifolia, Trigonella foenum-graecum, Ixora coccinea* and *Syzygium cumini* in equal amounts and the second Herb Blend comprises of herbs *Curcuma longa* and *Emblica officinalis* in a ratio of 1:2. Table 3 shows the ingredients and their amounts in percentage by weight. Table 3a shows the Proximate Composition of the dried Herbal Composition as analysed. The actives present in the Herbal Composition were measured using suitable methods such as Total tannins and Total organic acids as Gallic acid were measured by Titration, Total polyphenols by UV-visible spectroscopy and content of Gallic Acid, Ellagic acid and Curcuminoids was measured by HPLC.

TABLE 3

Components used for preparation of Herbal Composition

| Ingredients Name | Ingredients amount (% by wt.) |
| --- | --- |
| First Herb Blend | |
| *Curcuma longa* | 7.143 |
| *Emblica officinalis* | 7.143 |
| *Vernonia anthelmintica* | 7.143 |
| *Tinospora cordifolia* | 7.143 |
| *Trigonella foenum graecum* | 7.143 |
| *Ixora coccinea* | 7.143 |
| *Syzygium cumini* | 7.143 |
| Second Herb Blend | |
| *Curcuma longa* | 16.66 |
| *Emblica officinalis* | 33.33 |

TABLE 3a

Composition of the Actives in the Herbal Composition:

| Actives | % |
| --- | --- |
| Content of Total tannins | 17.6 |
| Content of Total organic acids as Gallic acid | 9.1 |
| Content of Total Polyphenols as Catechin | 18.2 |
| Gallic Acid | 3.3 |
| Ellagic Acid | 0.8 |
| Curcuminoids | 1.02 |

Example 4

In this example, representative herbal composition of present invention is described that is prepared and formulated into the herbal composition in paste form, wherein the first Herb Blend comprises of herbs *Curcuma longa, Emblica officinalis, Vernonia anthelmintica, Tinospora cordifolia, Trigonella foenum-graecum* and *Ixora coccinea* in equal amounts and the second Herb Blend comprises of herbs *Curcuma longa* and *Emblica officinalis* in a ratio of 1:3. Table 4 shows the ingredients and their amounts in percentage by weight. Table 4a shows the Proximate Composition of the dried Herbal Composition as analysed. The actives present in the Herbal Composition were measured using suitable methods such as Total tannins and Total organic acids as Gallic acid were measured by Titration. Total polyphenols by UV-visible spectroscopy and content of Gallic Acid, Ellagic acid and Curcuminoids was measured by HPLC.

TABLE 4

Components used for preparation of Herbal Composition

| Ingredients Name | Ingredients amount (% by wt.) |
| --- | --- |
| First Herb Blend | |
| *Curcuma longa* | 8.33 |
| *Emblica officinalis* | 8.33 |
| *Vernonia anthelmintica* | 8.33 |
| *Tinospora cordifolia* | 8.33 |
| *Trigonella foenum graecum* | 8.33 |
| *Ixora coccinea* | 8.33 |
| Second Herb Blend | |
| *Curcuma longa* | 12.50 |
| *Emblica officinalis* | 37.50 |

TABLE 4a

Composition of the Actives in the Herbal Composition:

| Actives | % |
| --- | --- |
| Content of Total tannins | 22.0 |
| Content of Total organic acids as Gallic acid | 11.6 |
| Content of Total Polyphenols as Catechin | 21.8 |
| Gallic Acid | 4.1 |
| Ellagic Acid | 0.92 |
| Curcuminoids | 1.05 |

Example 5

In this example, representative herbal composition of present invention is described that is prepared and formulated into the herbal composition in dry powder form, wherein the first Herb Blend comprises of herbs *Curcuma longa, Emblica officinalis, Vernonia anthelmintica, Tinospora cordifolia* and *Trigonella foenum-graecum* in equal amounts and the second Herb Blend comprises of herbs *Curcuma longa* and *Emblica officinalis* in a ratio of 1:3. Table 5 shows the ingredients and their amounts in percentage by weight. Table 5a shows the Proximate Composition of the dried Herbal Composition as analysed. The actives present in the Herbal Composition were measured using suitable methods such as Total tannins and Total organic acids as Gallic acid were measured by Titration, Total polyphenols by UV-visible spectroscopy and content of Gallic Acid, Ellagic acid and Curcuminoids was measured by HPLC.

TABLE 5

Components used for preparation of Herbal Composition

| Ingredients Name | Ingredients amount (% by wt.) |
|---|---|
| First Herb Blend | |
| Curcuma longa | 10 |
| Emblica officinalis | 10 |
| Vernonia anthelmintica | 10 |
| Tinospora cordifolia | 10 |
| Trigonella foenum graecum | 10 |
| Second Herb Blend | |
| Curcuma longa | 12.50 |
| Emblica officinalis | 37.50 |

TABLE 5a

Composition of the Actives in the Herbal Composition

| Actives | % |
|---|---|
| Content of Total tannins | 23.1 |
| Content of Total organic acids as Gallic acid | 12.4 |
| Content of Total Polyphenols as Catechin | 23.6 |
| Gallic Acid | 4.8 |
| Ellagic Acid | 1.0 |
| Curcuminoids | 1.21 |

Example 6

In this example, representative herbal composition of present invention is described that is prepared and formulated into the herbal composition in dry powder form, wherein the first Herb Blend comprises of herbs *Curcuma longa, Emblica officinalis, Vernonia anthelmintica* and *Tinospora cordifolia* in equal amounts and the second Herb Blend comprises of herbs *Curcuma longa* and *Emblica officinalis* in a ratio of 1:3. Table 6 shows the ingredients and their amounts in percentage by weight. Table 6a shows the Proximate Composition of the dried Herbal Composition as analysed. The actives present in the Herbal Composition were measured using suitable methods such as Total tannins and Total organic acids as Gallic acid were measured by Titration, Total polyphenols by UV-visible spectroscopy and content of Gallic Acid, Ellagic acid and Curcuminoids was measured by HPLC.

TABLE 6

Components used for preparation of Herbal Composition

| Ingredients Name | Ingredients amount (% by wt.) |
|---|---|
| First Herb Blend | |
| Curcuma longa | 12.50 |
| Emblica officinalis | 12.50 |
| Vernonia anthelmintica | 12.50 |
| Tinospora cordifolia | 12.50 |
| Second Herb Blend | |
| Curcuma longa | 12.50 |
| Emblica officinalis | 37.50 |

TABLE 6a

Composition of the Actives in the Herbal Composition:

| Actives | % |
|---|---|
| Content of Total tannins | 24.6 |
| Content of Total organic acids as Gallic acid | 12.9 |
| Content of Total Polyphenols as Catechin | 26.2 |
| Gallic Acid | 4.2 |
| Ellagic Acid | 1.1 |
| Curcuminoids | 1.18 |

Example 7

In this example, representative herbal composition of present invention is described that is prepared and formulated into the herbal composition in a paste form, wherein the first Herb Blend comprises of herbs *Curcuma longa, Emblica officinalis, Vernonia anthelmintica, Tinospora cordifolia, Trigonella foenum-graecum, Ixora coccinea* and *Syzygium cumini* in equal amounts and the second Herb Blend comprises of herbs *Curcuma longa* and *Emblica officinalis* in a ratio of 1:3. Table 7 shows the ingredients and their amounts in percentage by weight. Table 7a shows the Proximate Composition of the Herbal Composition in paste form. The actives present in the Herbal Composition were measured using suitable methods such as Total tannins and Total organic acids as Gallic acid were measured by Titration, Total polyphenols by UV-visible spectroscopy and content of Gallic Acid. Ellagic acid and Curcuminoids was measured by HPLC.

TABLE 7

Components used for preparation of Herbal Composition

| Ingredients Name | Ingredients amount (% by wt.) |
|---|---|
| First Herb Blend | |
| Curcuma longa | 7.143 |
| Emblica officinalis | 7.143 |
| Vernonia anthelmintica | 7.143 |
| Tinospora cordifolia | 7.143 |
| Trigonella foenum graecum | 7.143 |
| Ixora coccinea | 7.143 |
| Syzygium cumini | 7.143 |
| Second Herb Blend | |
| Curcuma longa | 12.50 |
| Emblica officinalis | 37.50 |

TABLE 7a

Composition of the Actives in the Herbal Composition:

| Actives | % |
|---|---|
| Content of Total tannins | 37.38 |
| Content of Total organic acids as Gallic acid | 24.08 |
| Content of Total Polyphenols as Catechin | 26.46 |
| Gallic Acid | 4.99 |
| Ellagic Acid | 1.38 |
| Total Curcuminoids | 1.28 |

Example 8

The Herbal composition as elaborated in Example 1 can be manufactured by the process as described below:

Raw Material—

100 Kg of raw material was taken with the ingredient proportion as under:

Herbs selected for first Herb Blend were *Curcuma longa*—7.14% *Emblica officinalis*—7.14% *Vernonia anthelmintica*—7.14% a *Tinospora cordifolia*—7.14% *Trigonella foenum-graecum*—7.14% *Ixora coccinea*—7.14% and *Syzygium cumini*—7.14%.

Herbs selected for second Herb Blend were—*Curcuma longa*—12.50% *Emblica officinalis*—37.50%.

Processing—

The herbs of first Herb Blend were pulverized and sifted. The pulverized herbs of first herb blend were then extracted using hydro-alcohol extraction process. The herbs are extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a first Extract Solution (930 to 970 L). The filter medium could be a 15 micron filter cloth. The herbs of second Herb Blend were separately pulverized and sifted and these herbs of second Herb Blend were extracted using a solvent at reflux or under circulation at 75° C. for 2 hours. The ratio of raw herbs and solvent used is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a second Extract Solution (780 to 810 L). The filter medium could be a 15 micron filter cloth. The first Extract Solution and second Extract Solution were then mixed in equal quantities and distilled at a temperature of 60° C.-65° C. and further concentrated at a temperature of 70° C.-75° C. under vacuum at 400 to 550 mmHg pressure to obtain a concentrated Extract Mix having a Total Solids content of 50%±2%. The concentrated Extract mix was then blended with a suitable diluent such as Cellulose powder which was then further dried in a Fluid Bed dryer or a Tray drier at a temperature of 52° C.-57° C. for a time period of 2.5 hrs to 3 hrs. to obtain the herbal composition in powder form. This dried Herbal composition was then further milled and sifted through a 40# sieve and blended in a blender to obtain a uniform powder (quantity 75 Kg±2 Kg). The Actives present in the powder were 53.1% and 46.9% diluents were present in the finished product.

Table 8 shows the Proximate Composition of the Herbal Composition in powder form. The actives present in the Herbal Composition were measured using suitable methods such as Total tannins and Total organic acids as Gallic acid were measured by Titration, Total polyphenols by UV-visible spectroscopy and content of Gallic Acid, Ellagic acid and Curcuminoids was measured by HPLC.

TABLE 8

Composition of the Actives in the Herbal Composition:

| Actives | % |
| --- | --- |
| Content of Total tannins | 21.40 |
| Content of Total organic acids as Gallic acid | 11.28 |
| Content of Total Polyphenols as Catechin | 21.38 |
| Gallic Acid | 4.2 |
| Ellagic Acid | 0.86 |
| Curcuminoids | 0.96 |

Example 9

The Herbal composition as elaborated in Example 7 can be manufactured by the process as described below:

Raw Material—

100 Kg of raw material was taken with the ingredient proportion as under:

Herbs selected for first Herb Blend were *Curcuma longa*—7.14% *Emblica officinalis*—7.14% *Vernonia anthelmintica*—7.14% *Tinospora cordifolia*—7.14% *Trigonella foenum-graecum*—7.14% *Ixora coccinea*—7.14% and *Syzygium cumini*—7.14%.

Herbs selected for second Herb Blend were—*Curcuma longa*—12.50% *Emblica officinalis*—37.50%

Processing—

The herbs of first Herb Blend were pulverized and sifted. The pulverized herbs of first herb blend were then extracted using hydro-alcohol extraction process. The herbs are extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a first Extract Solution (930 to 970 L). The filter medium could be a 15 micron filter cloth. The herbs of second Herb Blend were separately pulverized and sifted and these herbs of second Herb Blend were extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a second Extract Solution (780 to 810 L). The filter medium could be a 15 micron filter cloth. The first Extract Solution and the second Extract Solution were then mixed in equal quantities and distilled at a temperature of 60° C.-65° C. and further concentrated at a temperature of 70° C.-75° C. under vacuum at 400 to 550 mmHg pressure to obtain a concentrated Extract Mix having a Total Solids content of 70%±3%. The concentrated Extract mix was then blended with a suitable diluent such as water and preservatives to obtain the herbal composition in paste form. The diluents such as water were added in an amount of approximately 27-30% and preservatives were added in an amount of approximately 0.15-0.25%. The Proximate composition of the finished product was then analysed. Table 9 shows the Proximate Composition of the Herbal Composition in paste form. The actives present in the Herbal Composition were measured using suitable methods such as Total tannins and Total organic acids as Gallic acid were measured by Titration, Total polyphenols by UV-visible spectroscopy and content of Gallic Acid, Ellagic acid and Curcuminoids was measured by HPLC.

TABLE 9

Composition of the Actives in the Herbal Composition:

| Actives | % |
|---|---|
| Content of Total tannins | 36.20 |
| Content of Total organic acids as Gallic acid | 23.38 |
| Content of Total Polyphenols as Catechin | 25.70 |
| Gallic Acid | 5.22 |
| Ellagic Acid | 1.42 |
| Curcuminoids | 1.39 |

Example 10

The Herbal composition as elaborated in Example 2 can be manufactured by the process as described below:

Raw Material—

100 Kg of raw material was taken with the ingredient proportion as under:

Herbs selected for first Herb Blend were *Curcuma longa*—7.14% *Emblica officinalis*—7.14% *Vernonia anthelmintica*—7.14% *Tinospora cordifolia*—7.14% *Trigonella foenum-graecum*—7.14% *Ixora coccinea*—7.14% and *Syzygium cumini*—7.14%.

Herbs selected for second Herb Blend were—*Curcuma longa*—25.0% *Emblica officinalis*—25.0%

Processing—

The herbs of first Herb Blend were pulverized and sifted. The pulverized herbs of first herb blend were then extracted using hydro-alcohol extraction process. The herbs are extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a first Extract Solution (930 to 970 L). The filter medium could be a 15 micron filter cloth. The herbs of second Herb Blend were separately pulverized and sifted and these herbs of second Herb Blend were extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a second Extract Solution (780 to 810 L). The filter medium could be a 15 micron filter cloth. The first Extract Solution and second Extract Solution were then mixed and distilled at a temperature of 60° C.-65° C. and further concentrated at a temperature of 70° C.-75° C. under vacuum at 400 to 550 mmHg pressure to obtain a concentrated Extract Mix having a Total Solids content of 50%±2%. The concentrated Extract mix was then blended with a suitable diluent such as Cellulose powder which was then further dried in a Fluid Bed dryer or a Tray drier at a temperature of 52° C.-57° C. for a time period of 2.5 hrs to 3 hrs. to obtain the herbal composition in powder form. This dried Herbal composition was then further milled and sifted through a 40# sieve and blended in a blender to obtain a uniform powder (quantity 75 Kg±2 Kg). The Actives present in the powder were 51.8% and 48.2% diluents were present in the finished product.

Table 10 shows the Proximate Composition of the Herbal Composition in powder form. The actives present in the Herbal Composition were measured using suitable methods such as Total tannins and Total organic acids as Gallic acid were measured by Titration, Total polyphenols by UV-visible spectroscopy and content of Gallic Acid, Ellagic acid and Curcuminoids was measured by HPLC.

TABLE 10

Composition of the Actives in the Herbal Composition:

| Actives | % |
|---|---|
| Content of Total tannins | 15.0 |
| Content of Total organic acids as Gallic acid | 8.6 |
| Content of Total Polyphenols as Catechin | 15.8 |
| Gallic Acid | 2.9 |
| Ellagic Acid | 0.68 |
| Curcuminoids | 1.33 |

Example 11

The Herbal composition as elaborated in Example 3 can be manufactured by the process as described below:

Raw Material—100 Kg of raw material was taken with the ingredient proportion as under:

Herbs selected for first Herb Blend were *Curcuma longa*—7.14% *Emblica officinalis*—7.14% *Vernonia anthelmintica*—7.14% *Tinospora cordifolia*—7.14% *Trigonella foenum-graecum*—7.14% *Ixora coccinea*—7.14% and *Syzygium cumini*—7.14%.

Herbs selected for second Herb Blend were—*Curcuma longa*—16.66% *Emblica officinalis*—33.33%

Processing—

The herbs of first Herb Blend were pulverized and sifted. The pulverized herbs of first herb blend were then extracted using hydro-alcohol extraction process. The herbs are extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a first Extract Solution (930 to 970 L). The filter medium could be a 15 micron filter cloth. The herbs of second Herb Blend were separately pulverized and sifted and these herbs of second Herb Blend were extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a second Extract Solution (780 to 810 L). The filter medium could be a 15 micron filter cloth. The first Extract Solution and second Extract Solution were then mixed and distilled at a temperature of 60° C.-65° C. and further concentrated at a temperature of 70° C.-75° C. under vacuum at 400 to 550 mmHg pressure to obtain a concentrated Extract Mix having a Total Solids content of 50%±2%. The concentrated Extract mix was then blended with a suitable diluent such as Cellulose powder which was then further dried in a Fluid Bed dryer or a Tray drier at a temperature of 52° C.-57° C. for a time period of 2.5 hrs to 3 hrs. to obtain the herbal composition in powder form. This dried Herbal composition was then further milled and sifted through a 40# sieve and blended in a blender to obtain a uniform powder (quantity 75 Kg±2 Kg). The Actives present in the powder were 52.2% and 47.8% diluents were present in the finished product.

Table 11 shows the Proximate Composition of the Herbal Composition. The actives present in the Herbal Composition were measured using suitable methods such as Total tannins and Total organic acids as Gallic acid were measured by Titration, Total polyphenols by UV-visible spectroscopy and content of Gallic Acid, Ellagic acid and Curcuminoids was measured by HPLC.

TABLE 11

Composition of the Actives in the Herbal Composition:

| Actives | % |
| --- | --- |
| Content of Total tannins | 17.9 |
| Content of Total organic acids as Gallic acid | 9.6 |
| Content of Total Polyphenols as Catechin | 18.8 |
| Gallic Acid | 3.1 |
| Ellagic Acid | 0.8 |
| Curcuminoids | 1.06 |

Example 12

The Herbal compositions as elaborated in Example 4 can be manufactured by the process as described below:

Raw Material—

100 Kg of raw material was taken with the ingredient proportion as under:

Herbs selected for first Herb Blend were *Curcuma longa*—8.33% *Emblica officinalis*—8.33% *Vernonia anthelmintica*—8.33% *Tinospora cordifolia*—8.33% *Trigonella foenum-graecum*—8.33% and *Ixora coccinea*—8.33%

Herbs selected for second Herb Blend were—*Curcuma longa*—12.50% *Emblica officinalis*—37.50%

Processing—

The herbs of first Herb Blend were pulverized and sifted. The pulverized herbs of first herb blend were then extracted using hydro-alcohol extraction process. The herbs are extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a first Extract Solution (930 L to 970 L). The filter medium could be a 15 micron filter cloth. The herbs of second Herb Blend were separately pulverized and sifted and these herbs of second Herb Blend were extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain a second Extract Solution (780 L to 810 L). The filter medium could be a 15 micron filter cloth. The first Extract Solution and the second Extract Solution were then mixed distilled at a temperature of 60° C.-65° C. and further concentrated at a temperature of 70° C.-75° C. under vacuum at 400 to 550 mmHg pressure to obtain a concentrated Extract Mix having a Total Solids content of 70%±3%. The concentrated Extract mix was then blended with a suitable diluent such as water and preservatives to obtain the herbal composition in paste form. The diluents such as water were added in an amount of approximately 27-30% and preservatives were added in an amount of approximately 0.15-0.25%. The Proximate composition of the finished product was then analysed.

Table 12 shows the Proximate Composition of the Herbal Composition in paste form. The actives present in the Herbal Composition were measured using suitable methods such as Total tannins and Total organic acids as Gallic acid were measured by Titration, Total polyphenols by UV-visible spectroscopy and content of Gallic Acid, ellagic acid and Curcuminoids was measured by HPLC.

TABLE 12

Composition of the Actives in the Herbal Composition:

| Actives | % |
| --- | --- |
| Content of Total tannins | 40.48 |
| Content of Total organic acids as Gallic acid | 24.20 |
| Content of Total Polyphenols as Catechin | 28.34 |
| Gallic Acid | 5.33 |
| Ellagic Acid | 1.43 |
| Curcuminoids | 1.37 |

Example 13

In this example, representative herbal composition of present invention is described that is prepared and formulated into the herbal composition in a dry powder form, wherein the single Herb Blend comprises of herbs *Tinospora cordifolia, Trigonella foenum-graecum, Ixora coccinea* and *Syzygium cumini* in equal amounts. Table 13 shows the ingredients and their amounts in percentage by weight. Table 13a shows the Proximate Composition of the Herbal Composition. The actives present in the Herbal Composition were measured using suitable methods such as Total tannins and Total organic acids as Gallic acid were measured by Titration, Total polyphenols by UV-visible spectroscopy and content of Gallic Acid, Ellagic acid was measured by HPLC.

The Herbal composition as elaborated above can be manufactured by the process as described below:

Raw Material—

100 Kg of raw material was taken with the ingredient proportion as under:

Herbs selected for the single Herb Blend were *Tinospora cordifolia*—25% *Trigonella foenum-graecum*—25%, *Ixora coccinea*—25% and *Syzygium cumini*—25%

The herbs of the single Herb Blend were pulverized and sifted. The pulverized herbs of the herb blend were then extracted using hydro-alcohol extraction process. The herbs are extracted using a solvent at reflux or under circulation at 75° C. for 2 hours. The ratio of raw herbs and solvent used in extraction is 1:10. 1000 L of solvent was used for hydro-alcohol extraction comprising alcohol and water in a ratio of 70:30. The alcohol used may be selected from methyl alcohol, ethyl alcohol and iso-propyl alcohol, preferably ethyl alcohol. The extract was then filtered through a suitable filter medium under gravity pressure to obtain an Extract Solution (930 to 970 L). The filter medium could be a 15 micron filter cloth. The Extract Solution was then distilled at a temperature of 60° C.-65° C. and further concentrated at a temperature of 70° C.-75° C. under vacuum at 400 to 550 mmHg pressure to obtain a concentrated Extract having a Total Solids content of 50%±2%. The concentrated Extract was then blended with a suitable diluent such as Cellulose powder which was then further dried in a Fluid Bed dryer or a Tray drier at a temperature of 52° C.-57° C. for a time period of 2.5 hrs to 3 hrs. to obtain the herbal composition in powder form. This dried Herbal composition was then further milled and sifted through a 40# sieve and blended in a blender to obtain a uniform powder (quantity 75 Kg±2 Kg). The Actives present in the powder were 52.5% and 47.5% diluents were present in the finished product.

TABLE 13

Components used for preparation of Herbal Composition

| Ingredients Name | Ingredients amount (% by wt.) |
|---|---|
| Herb Blend | |
| Tinospora cordifolia | 25.0 |
| Trigonella foenum graecum | 25.0 |
| Ixora coccinea | 25.0 |
| Syzygium cumini | 25.0 |

TABLE 13a

Composition of the Actives in the Herbal Composition:

| Actives | % |
|---|---|
| Content of Total tannins | 20.5 |
| Content of Total organic acids as Gallic acid | 9.20 |
| Content of Total Polyphenols as Catechin | 22.1 |
| Gallic Acid | 2.5 |
| Ellagic Acid | 0.45 |

Example 14

In Vitro Glucose Uptake Study to Assess the Efficacy of the Herbal Composition Vs the Raw Herbs Objective:

The purpose of this study was to assess the glucose uptake potential of test substance in vitro.

Test System:

L6 cell line (Rat, skeletal muscle cells)

Test Culture Preparation:

Cell lines were cultured in DMEM media supplemented with 10% inactivated Fetal Bovine Serum (FBS), penicillin (100 IU/ml), streptomycin (100 ∝g/ml) and amphotericin B (5 ∝g/ml) in a humidified atmosphere of 5% $CO_2$ at 37° C. until confluent. The cells were dissociated with TPVG solution (0.2% trypsin, 0.02% EDTA, 0.05% glucose in PBS). The stock cultures were grown in 25 $cm^2$ culture flasks and all experiments were carried out in 96 microtitre plates.

Experiments:

Preparation of Test Doses—

For studies, each weighed test drugs were separately dissolved in distilled DMSO and volume was made up with DMEM supplemented with 2% inactivated FBS to obtain a stock solution of 1 mg/ml concentration and sterilized by filtration. Serial two fold dilutions were done from this to perform cytotoxic studies.

Reference Standards—

Standard formulations/drugs available in market were employed as reference formulations in the experiment.

In Vitro Glucose Uptake Study

Glucose Uptake Assay—

Glucose uptake activity of test substance was determined in differentiated L6 cells. In brief, the 24 hr cell cultures with 70-80% confluency in 40 mm petri plates were allowed to differentiate by maintaining in DMEM with 2% FBS for 4-6 days. The extent of differentiation to be established by observing multinucleation of cells. The differentiated cells were serum starved overnight and at the time of experiment, cells were washed with HEPES buffered Krebs Ringer Phosphate solution (KRP buffer) once and incubated with KRP buffer with 0.1% BSA for 30 min at 37° C. Cells were treated with different non-toxic concentrations of test substance and standard for 30 min along with negative controls at 37° C. 20 µl of D-glucose solution was added simultaneously to each well and incubated at 37° C. for 30 min. After incubation, the uptake of the glucose was terminated by aspiration of solutions from wells and washing thrice with ice-cold KRP buffer solution. Lyse the cells with 0.1M NaOH solution and an aliquot of cell lysates was used to measure the cell-associated glucose. The glucose levels in cell lysates was measured using glucose assay kit. Three independent experimental values in duplicates were taken to determine the percentage enhancement of glucose uptake over controls.

Observations—

The modulatory effect of test substance on glucose uptake in treated cells over control group was determined and expressed as percentage glucose uptake over control. The observed results are shown in Table 14 and 14a.

TABLE 14

In vitro glucose uptake results for Herbal Composition of Example 1 in L-6 cell line

| S. No. | Sample | Glucose uptake over control (%) at Concentration (µg/ml) | | | | |
|---|---|---|---|---|---|---|
| | | 1000 (µg/ml) | 500 (µg/ml) | 250 (µg/ml) | 100 (µg/ml) | 10 (µg/ml) |
| 1. | Curcuma Longa (CL) | 57.5 | 55 | 37.5 | 35.83 | 4.17 |
| 2. | Emblica officinalis (EO) | 25 | 15.83 | 5.83 | 0.83 | 0.83 |
| 3. | Vernonia anthelmintica (VA) | 66.67 | 17.5 | 15 | 5 | 3.33 |
| 4. | Tinospora cordifolia (TC) | 90 | 85.83 | 75.83 | 64.17 | 0.83 |
| 5. | Trigonella foenum-graecum (TFG) | 88.33 | 52.5 | 42.5 | 46.67 | 12.5 |

TABLE 14-continued

In vitro glucose uptake results for Herbal Composition of Example 1 in L-6 cell line

| S. No. | Sample | Glucose uptake over control (%) at Concentration (µg/ml) | | | | |
|---|---|---|---|---|---|---|
| | | 1000 (µg/ml) | 500 (µg/ml) | 250 (µg/ml) | 100 (µg/ml) | 10 (µg/ml) |
| 6. | Ixora coccinea (IO) | 22 | 12.5 | 10 | 4 | 0 |
| 7. | Syzygium cumini (SC) | 78.65 | 45 | 18.15 | 14 | 4 |
| 8. | Herbal Composition of Example 1 Control | 174 | 114.25 | 112.15 | 96 | 8 |
| 9. | Market Sample 1 | — | 96 | 70 | 48 | — |
| 10. | Market Sample 2 | — | 142 | 116 | 102 | — |

Results—

The herbal composition of Example 1 demonstrates dose dependent glucose uptake and highest activity when compared to individual ingredients. Also the Herbal Composition of Example 1 exhibits synergistic activity showing higher glucose uptake than the individual herbs when tested at different concentrations (1000, 500, 250, 100 and 10 µg/ml). Further, the herbal composition also exhibits higher glucose uptake than the market sample when tested at 500, 250 and 100 µg/ml concentrations.

TABLE 14a

In vitro glucose uptake results for Herbal Composition in L-6 cell line

| S. No. | Sample | Glucose uptake over control (%) at Concentration of 1000 µg/ml |
|---|---|---|
| 1. | Curcuma Longa (CL) | 57.5 |
| 2 | Emblica officinalis (EO) | 25 |
| 3. | Vernonia anthelmintica (VA) | 66.67 |
| 4. | Tinospora cordifolia (TC) | 90 |
| 5. | Trigonella foenum-graecum (TFG) | 88.33 |
| 6. | Ixora coccinea (IO) | 22 |
| 7. | Syzygium cumini (SC) | 78.65 |
| 8. | Herbal Composition of Example 4 | 142.69 |
| 9. | Herbal Composition of Example 5 | 112 |
| 10. | Herbal Composition of Example 6 | 123 |
| 11. | Herbal Composition of Example 13 | 135.14 |

Results:

The herbal composition of Examples 4, 5, 6 and 13 demonstrates synergistic activity when compared to individual ingredients/herbs at a concentration of 1000 µg/ml.

The herbal composition of Example 4, which is comprising of herbs selected from Curcuma longa, Emblica officinalis, Vernonia anthelmintica, Tinospora cordifolia, Trigonella foenum-graecum and Ixora coccinea demonstrates synergistic activity when compared to individual ingredients/herbs at a concentration of 1000 µg/ml.

The herbal composition of Example 5, which is comprising of herbs selected from Curcuma longa, Emblica officinalis, Vernonia anthelmintica, Tinospora cordifolia and Trigonella foenum-graecum demonstrates synergistic activity when compared to individual ingredients/herbs at a concentration of 1000 µg/ml.

The herbal composition of Example 6, which is comprising of herbs selected from Curcuma longa, Emblica officinalis, Vernonia anthelmintica, and Tinospora cordifolia demonstrates synergistic activity when compared to individual ingredients/herbs at a concentration of 1000 µg/ml.

The herbal composition of Example 13 which is comprising of herbs selected from Tinospora cordifolia, Trigonella foenum-graecum, Ixora coccinea and Syzygium cumini demonstrates synergistic activity when compared to individual ingredients/herbs at a concentration of 1000 µg/ml.

Further, the said herbal compositions also exhibit higher glucose uptake than the market sample when tested at 1000 µg/ml concentrations.

Example 15

In Vivo Synergy of Herbal Composition in the C57BL/6 Mice Model

The Model—

High Fat Diet Studies—

Nutrition strongly modulates risk factors in the development of metabolic disorders and chronic diseases, including obesity, metabolic syndrome, type 2 diabetes mellitus, and cardiovascular diseases. The maintenance of metabolic homeostasis relies on the balanced intake of nutrients from food. Dietary formulations with strong nutrient imbalances can lead to metabolic disorders, with lipids and sugars playing a prominent role. In order to gain a greater understanding of human metabolic disorders, mice are the commonly used models because they readily develop these pathologies, when provided with an appropriate high fat diet. A high fat diet causes weight increase and insulin resistance in C57BL/6 mice. These mice are sensitive to the effect of the diet which is similar to human obesity. These mice on a high fat diet develop severe obesity, hyperinsulinemia and high mesenteric fat cells. Late stage animals also develop hyperglycemia. Hence this model is useful for the screening of potential anti-obesity drugs. The high fat diet contains 34.3% fat or 60% Kcal Fat while the normal diet contains 6.2% fat or 18 Kcal of fat.

Objective—

The objective of this study was to observe the effects of the Herbal Composition on body weight and food consumption for 60 days in male C57BL/6 mice fed on a 34.3% fat diet, followed by a 30 day period to study the reversal of drug-induced effects.

Testing Procedure—

The Control group of mice were fed an equal volume of normal diet with 6.2% fat. A second Control group of mice were fed an equal volume of High Fat diet with 34.3% fat. The treatment groups of mice were orally administered with the Herbal Composition of the present invention at a dose of 5.71 mg/kg/day, the human equivalent dose of 400 mg/70 kg. At the end of treatment for 60 days, the drug treatments were discontinued and the mice maintained on the same diet for another 30 days. The body weights were measured twice a week during this period. Oral Glucose Tolerance Test was conducted at the end of drug treatment (day 60) and then at the end of treatment reversal period (day 90).

Results—

Figure 2:
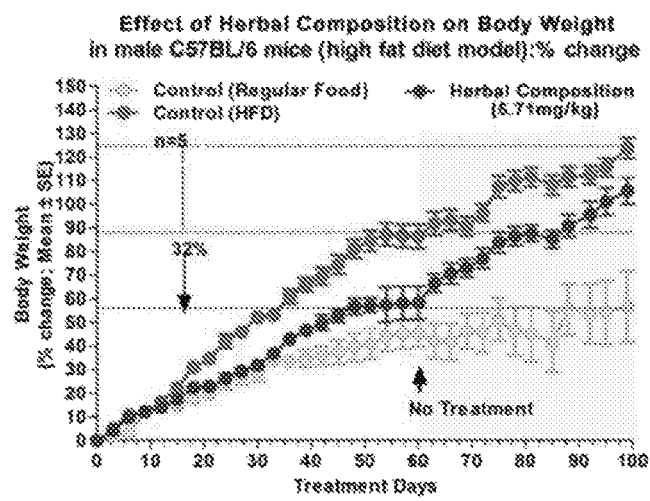
FIG. 2 shows the comparison of effect on body weight in Male C57BL/6 Mice when fed with the Herbal Composition, High Fat Diet (HFD) and Control Diet for a period of 90 days.

1. Effect on Body weight gain—The results are as depicted in FIG. 2 and it could be concluded that the herbal composition of the present invention prevents body weight gain on a continued therapy basis.

Figure 3:
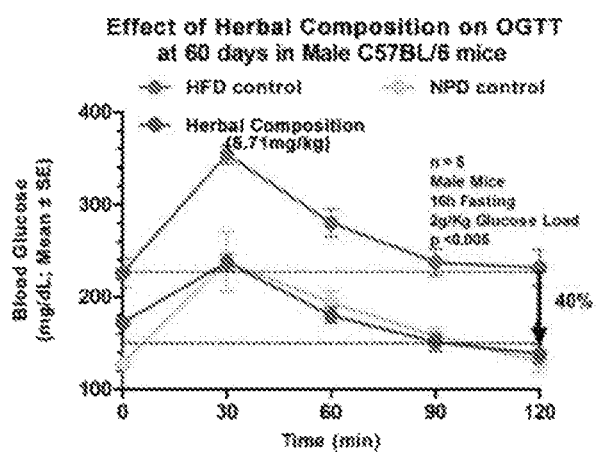
FIG. 3 shows the comparison of results of Oral Glucose Tolerance Test (OGTT) at 60 days in Male C57BL/6 Mice when fed with the Herbal Composition, High Fat Diet (HFD) and Control Diet for a period of 60 days.
Figure 4:
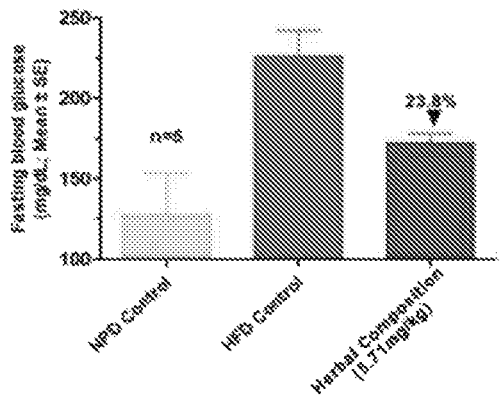
FIG. 4 shows the comparison of results of Fasting Blood Glucose at 60 days in Male C57BL/6 Mice when fed with the Herbal Composition, High Fat Diet (HFD) and Control Diet for a period of 60 days.
Figure 5:
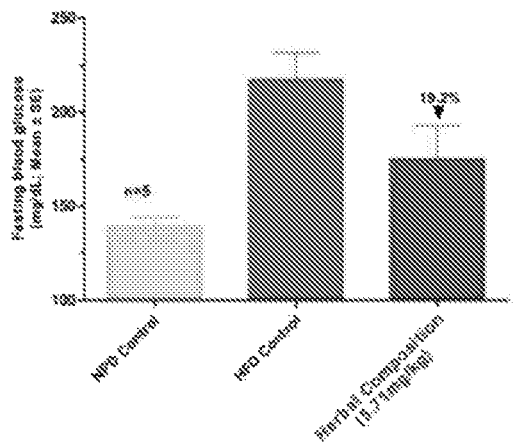
FIG. 5 shows the comparison of results of Fasting Blood Glucose at 60 days treatment and 30 days recovery in Male C57BL/6 Mice when fed with the Herbal Composition, High Fat Diet (HFD) and Control Diet for a period of 60 days.

2. The results of Oral Glucose Tolerance Test, Fasting Blood Glucose at 60 days and Fasting Blood Glucose at 60 days treatment and 30 days recovery are as depicted in FIGS. 3, 4 and 5. It could be concluded that the herbal composition of the present invention decreases serum glucose, fasting blood glucose and oral glucose tolerance test (OGTT).

Example 16

In Vivo Synergy of Herbal Composition in the Db/Db Mice Model

The Model:

db/db Mice Studies—

The db gene is an autosomal recessive mutation in C57BL/KsJ inbred strain. There is a defect in the Leptin Gene. These animals show an extreme, early-onset obesity syndrome and hyperglycemia (over 300 mg/dl) in the fed state by 6 weeks of age, which will increase over time. Like human subjects with uncontrolled NIDDM (Noninsulin-dependent diabetes mellitus), these db/db mice also experience polydipsia, polyuria, and glycosuria during their hyperglycemic stage but, they still gain weight during the first 3 months of life if fed ad libitium. Prior to and for 6-10 week after the onset of frank diabetes, db/db mice consistently show increase in overall adiposity, thermoregulatory defects and functional sterility. Hypertriglyceridemia and hypercholesterolemia are also more severe. Homozygotes of this strain are hyperphagic, obese, and after initial mild hyperglycemia they develop severe hyperglycemia exceeding 500 mg/dL. Increased plasma insulin concentration is observed as early as 10 days of age and reaches a peak—6 to 10 times by 2 to 3 months of age and then drops. At the same time, blood glucose concentration rapidly rises to over 400 mg/dL and remains elevated until death by 5 to 8 months. Prior to the drop in plasma insulin concentration, the most consistent morphological feature of the islets of Langerhans is hyperplasia and hypertrophy of beta cells in an attempt to produce sufficient insulin to control blood sugar concentration at physiological levels. The plasma concentration of glucagon and pancreatic glucagon content are increased. Obesity, hyperglycemia, hyperinsulinemia and increased levels of triglycerides and Free-Fatty Acids (FFA) characterizes this form of diabetes. These findings are similar to those that are encountered in many patients with type-II diabetes. Another feature of db/db mouse, which has, at least to some extent, a human counterpart, is the decline in beta cell function that occurs with increasing duration of the diabetes state. The db/db mouse may thus be a suitable model for that type of human NIDDM that is couple to obesity and insulin resistance.

Objective—

The objective of this study was to observe the effects of the Herbal Composition of the present invention on body weight and blood glucose in 30 days in db/db mice fed on a normal diet of 6.2% fat or 18 Kcal of fat.

Testing Procedures—

Based on their blood glucose values the mice were randomized into control and treatment groups. The treatment groups of mice were administered the Herbal composition of the present invention at 50 mg/kg/day, p.o. Body weights and glucose levels were measured twice a week. Fasting blood glucose and Oral glucose tolerance test was conducted at the end of the study. (Day 30)

Results—

Figure 6:
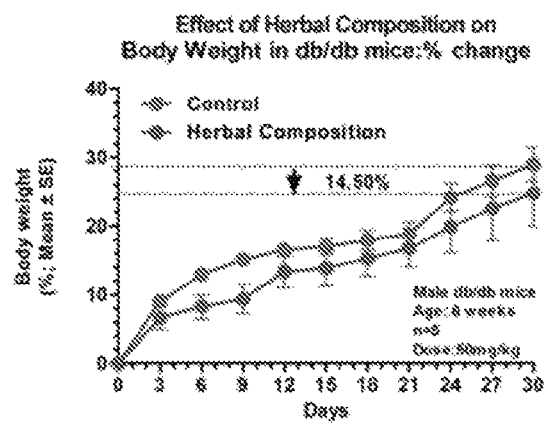
FIG. 6 shows the comparison of effect on body weight of db/db mice when fed with the herbal composition and Control Diet for a period of 30 days.

1. Effect on Body weight gain—The results are as depicted in FIG. 6 and it could be concluded that the herbal composition of the present invention arrests body weight gain.

Figure 7:
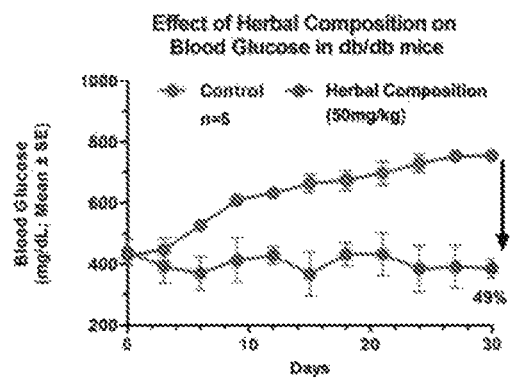
FIG. 7 shows the comparison of effect on Blood Glucose of db/db mice when fed with the herbal composition and Control Diet for a period of 30 days.
Figure 8:
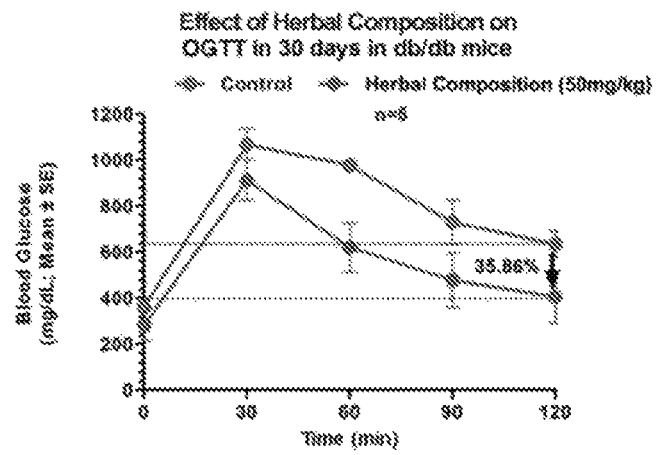
FIG. 8 shows the comparison of results of Oral Glucose Tolerance Test (OGTT) at 30 days in db/db mice when fed with the herbal composition and Control Diet for a period of 30 days.
Figure 9:
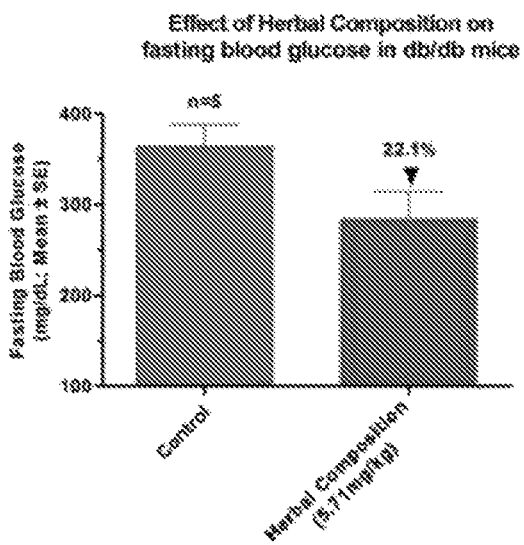
FIG. 9 shows the comparison of results of Fasting Blood Glucose at 30 days in db/db mice when fed with the herbal composition and Control Diet for a period of 30 days.

2. The results of effect on Blood Glucose, Oral Glucose Tolerance Test and Fasting Blood Glucose at 30 days are as depicted in FIGS. 7, 8 and 9. It could be concluded that the herbal composition of the present invention decreases serum glucose, oral glucose tolerance test (OGTT) and fasting blood glucose.

Example 17

In Vivo Synergy of Herbal Composition in the Hamster Model

The Model:

Hamster Study—

Atherosclerosis is a serious health condition and cause of clinical complications of stroke and heart failure. The Golden Syrian hamster is sensitive to high-fat cholesterol-supplemented diet. The hamster carries a significant portion of its plasma cholesterol in the LDL lipoprotein fraction and is thus closer to humans than to rodents. Hamster is a good model for the study of lipid metabolism with high-fat cholesterol-supplemented diet. Cholesterol-fed hamsters develop mild atherosclerosis. Hamsters fed a very-high (60%) fructose diet become insulin-resistant and have been used to study effects on insulin signalling and lipoprotein metabolism. The hamster is preferred species for diet-induced atherosclerosis studies due to its apparent low rate of endogenous cholesterol synthesis, receptor mediated uptake of low density lipoprotein cholesterol, presence of cholesteryl ester transfer protein activity, secretion of apolipoprotein (apo) B-100 from the liver and apo B-48 from the small intestine, and uptake of the majority of LDL-C via the LDL receptor pathway. The morphology of aortic foam cells and lesions in hamsters fed atherogenic diet was reported to be similar to human lesion.

The Objective—

The objective of this study was to study effect of the Herbal Composition of the present invention on triglycerides and glucose.

Testing Procedures—

Male Golden Syrian hamsters were procured from Simonsen Laboratories at 5 weeks of age. They were quarantined for 7 days and then randomized into vehicle and treatment groups consisting of Vehicle, and the Herbal composition of the present invention at the Human Equivalent Dose. The treatment group mice were treated on a diet consisting of 0.5% cholesterol, 11.5% corn oil, and 11.5% coconut oil. This diet was continued throughout the study. The hamsters were orally administered with the treatment formulation and vehicle daily. At the end of 30 days and 60 days, the hamsters were fasted overnight and blood collected by cardiac puncture. The fasting blood glucose and total serum triglycerides were measured.

Results—

Figures 11A, 11B:
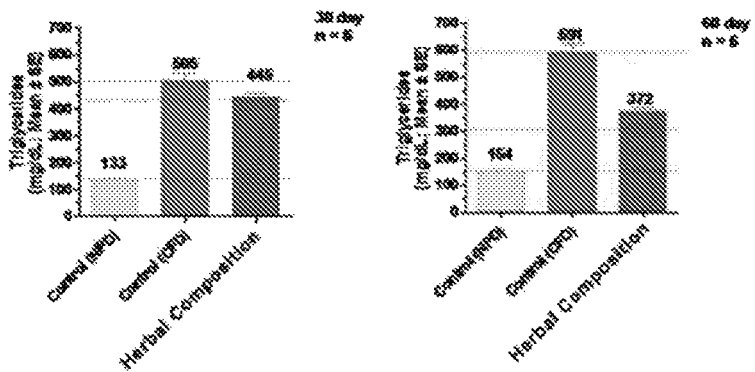
FIG. 11(a) shows the comparison of Total serum Triglycerides at 30 days in Hamsters when fed with the herbal composition, cholesterol fed diet and Control Diet for a period of 30 days.
FIG. 11(b) shows the comparison of Total serum Triglycerides at 60 days in Hamsters when fed with the herbal composition, cholesterol fed diet and Control Diet for a period of 60 days.

FIGS. 10 (a) and 10(b) depict the results of Fasting Blood Glucose at 30 and 60 days respectively while the FIGS. 11 (a) and 11(b) depict the results of Total Serum Triglycerides at 30 and 60 days respectively. It could be concluded that the herbal composition of the present invention exhibits a reasonable decrease in total serum triglyceride in 60 days treatment whereas it maintains the fasting blood glucose in 30 as well as 60 days treatment.

Example 18

In Vivo Synergy of Herbal Composition in Apo E (−/−) Study

The Model—

Apo E (−/−) Study—

Atherosclerosis is a serious health condition and cause of clinical complications of stroke and heart failure. ApoE (apoE) is a 34-kDA secreted protein synthesized in liver and macrophages. It is a ligand for cell-surface lipoprotein receptors and prevents atherosclerosis by clearing cholesterol-rich lipoproteins from plasma. The apoE (−/−) mouse model is used to test mechanisms of atherogenesis and apoE-driven atherosclerosis modulation. These include the effect of diet and drugs, the role of inflammation, oxidation, immunomodulation, coagulation, and plaque composition, as well as atheroma progression and regression. The apoE knockout mouse reproduces many of the features of human apoE deficiency and develops spontaneous atherosclerosis which is enhanced by a high-cholesterol diet to the extent that the animal exhibits xanthomas. This model has been used to determine the threshold of circulating apoE above which atherosclerosis develops and whether it is possible to distinguish between lipoprotein effects and effects related to other anti-atherogenic properties of apoE.

The Objective—

The objective of the study was to study the effect of Herbal Composition of the present invention in ApoE$^{(-/-)}$ mice.

Testing Procedures—

Male ApoE$^{(-/-)}$ mice were procured from Taconic Farms at 5 weeks of age. They were quarantined for 7 days and then randomized into groups consisting of Vehicle and Herbal Composition of the present invention at the Human Equivalent Dose. The treatment groups of mice were treated on a diet consisting of 21.2% fat. This diet was continued throughout the study. The mice were orally administered with the treatment formulation and vehicle daily. At the end of 90 days and 180 days, the mice were fasted overnight and blood collected by cardiac puncture. The total serum cholesterol was measured.

Results—

Figures 12A, 12B:
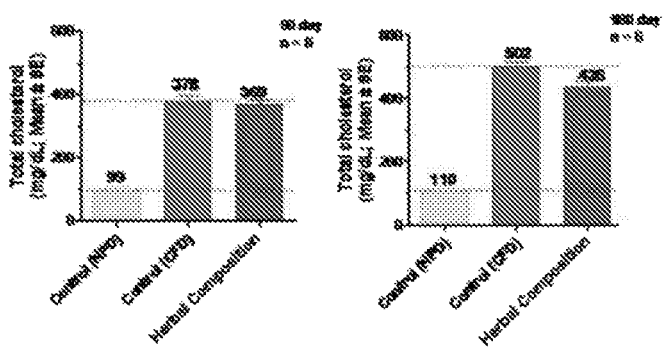
FIG. 12(b) shows the comparison of Total cholesterol at 180 days in Apo E(-/-) mice when fed with the herbal composition, cholesterol fed diet and Control Diet for a period of 180 days.

FIGS. 12 (a) and 12 (b) depict the results of Total Serum Cholesterol at 90 and 180 days respectively. It could be concluded that the herbal composition of the present invention exhibits reasonable reduction in serum cholesterol in 180 days.

Example 19

Toxicity Studies

Acute Toxicity Study in Mice

Objective—

Acute toxicity studies in animals are necessary for any drug development programme. The information obtained from these studies is useful in choosing doses for repeat-dose studies, providing preliminary identification of target organs toxicity, and revealing delayed toxicity. Acute toxicity studies may also aid in the selection of starting doses for Phase 1 clinical studies, and provide information relevant to acute overdosing. As per FDA-guidelines, acute toxicity studies are to be undertaken with a single administration of escalating doses of a test compound or drug. Following the administration, the animals are to be observed for 14 days for any behavioural abnormalities, fluctuations in body weight, morbidity and mortality. The objectives of this study were as to determine the acute toxic effects of the herbal composition at 1×, 10× and 100× of the Human Equivalent Doses.

Materials

Animals—

Male and female Swiss Webster mice at 6 weeks of age were procured from Simonsen Laboratories, Gilroy, Calif. They were housed in a rodent facility and maintained at a temperature of 22-24° C. with 12-hour light-dark cycle, and provided with food and water ad-libitum.

| Overview of Materials used in the study | |
|---|---|
| Item | Manufacturer/Supplier |
| The Herbal Composition of Example 1 | |
| Potable Water | Arrowhead Mountain Spring Water Co., USA |
| Weigh Balance (Model: BD1201) | Mettler Toledo, Switzerland |
| Weigh Balance (Model: A-200D) | Denver Instrument Company, USA |
| Sani Chips | Harlan Teklad, USA |
| Rodent Diet 2018 | Harlan Teklad, USA |
| Stainless Steel Gavage Needles | Popper & Sons, USA |
| 1 mL Sterile Disposable Syringes | Becton, Dickinson and Company, USA |

Methods—

On the day of the study the mice were weighed and randomized into 4 groups. Group I—control group was administered potable water. Group II—Treatment Group I was administered with the Herbal Composition of Example 1 at 100× of Human Equivalent Dose. Group III—Treatment Group II was administered with the Herbal Composition of Example 1 at 10× of Human Equivalent Dose. Group IV—Treatment Group III was administered with the Herbal Composition of Example 1 at 1× of Human Equivalent Dose.

Preparation of Dosing Solutions—

Based on human dose of 400 mg, 140 mg of the Herbal Composition of Example 1 was weighed and 2 mL of potable water was added to it. This dosage was labelled as Dose 100×. A 200 µL volume of Dose 100× when administered to the Group II Swiss Webster mice was equal to 100× of the human equivalent dose. The tube containing Dose 100× was vortexed for 10 seconds, a 200 µL aliquot transferred into another tube, and 1800 µL of potable water added to it. This dose was labelled as Dose 10×. A 200 µL dose of Dose 10× when administered to the Group III Swiss Webster mice was equal to 10× of the human equivalent dose. The tube containing Dose 10× was vortexed for 10 seconds, a 200 µL aliquot transferred into another tube, and 1800 µL of potable water added to it. This dose was labelled as Dose 1×. A 200 µL of Dose 1× when administered to Group IV Swiss Webster mice was equal to 1× of the human equivalent dose. Mice of Group I were administered with 200 µL of potable water.

Behavioural Observations—

Following oral administration of water and the Herbal Composition of Example 1, the mice were observed for tremors, sedation, convulsion, catatonia, alertness, muscle spasm, cyanosis, writhing, irritability, ptosis and diarrhoea at 30 minutes, 1, 2 and 4 hours, and then once daily till day 15.

Termination—

On day 15 the mice were weighed and euthanized by carbon dioxide asphyxiation. Blood was collected by cardiac puncture and transferred into separate tubes containing EDTA and sodium heparin and maintained on ice. Blood in heparinised tubes were centrifuged in a refrigerated microcentrifuge at 5000 RPM for 5 minutes, temperature 2-4° C. The blood tubes were analyzed for clinical chemistry (superchemistry), complete blood counts and differential counts. The major organs heart, liver, kidneys, spleen, testes, ovary and brain were dissected out and weighed. Heart, liver and kidneys were preserved in 10% formalin and fixed by haematoxylin and eosin stain for histological evaluation.

Results—

The following conclusions were derived from oral administration of the the Herbal Composition of Example 1 at three different doses (1×, 10× and 100×) of Human Equivalent Dose (HED) to male and female Swiss Webster mice in a non-GLP acute toxicity study:

1. Body Weight Measurements—

No changes in body weight were observed when Herbal Composition of Example 1 was delivered orally, compared with the control group of mice.

2. Behavioural Parameters—

No alterations in behavioural parameters were observed when compared with the control group of male and female mice.

3. Organ Weight Measurements—

No difference in the weights of brain, heart, liver, kidneys, spleen, testes and ovaries was observed between treated and untreated group of male and female mice.

4. Clinical Chemistry—

Acute dose treatment of Herbal composition of Example 1 did not alter clinical chemistry on 22 parameters as compared to control standards (separately generated by NRL on exact specific strain).

5. Complete Blood Counts (CBC)—

No significant change in 13 different complete blood counts was observed as compared to control group and standards (separately generated by NRL on exact specific strain).

6. Histology—

No significant differences were observed in the histological evaluation between the vehicle and treatment groups While particular embodiments of the herbal composition of present invention have been illustrated and described, it would be obvious to those skilled in the art that various other changes and modifications can be made within departing from the spirit and scope of the invention. It is thereof intended to cover in the appended claims such changes and modifications that are within the scope of the invention.

REFERENCES

1. Metabolic syndrome pandemic, Grundy Arterioscler Thromb Vasc Biol. 2008; 28:629-636.
2. 2002 Third report of the National Cholesterol Education Program (NCEP) expert panel on detection, evaluation, and treatment of high blood cholesterol in adults (Adult Treatment Panel III). Final Report. Circulation 106:3143-3421)
3. Grundy S M, Cleeman J I, Daniels S R, Donato K A, Eckel R H, Franklin B A, Gordon D J, Krauss R M, Savage P J, Smith Jr S C, Spertus J A, Costa F 2005 Diagnosis and management of the metabolic syndrome. An American Heart Association/National Heart, Lung, and Blood Institute Scientific Statement. Circulation 112: 2735-2752
4. Alberti KGMM, Zimmet P, Shaw J 2005 IDF Epidemiology Task Force Con-sensus Group. Lancet 66:1059-1062
5. Grundy S M. Metabolic syndrome: a multiplex cardiovascular risk factor. J Clin Endocrinol Metab. 2007; 92:399-404.
6. Park Y W, Zhu S, Palaniappan L, Heshka S, Carnethon M R, Heymsfield S B 2003 The metabolic syndrome: prevalence and associated risk factor findings in the US population from the Third National Health and Nutrition Exami-nation Survey, 1988-1994. Arch Intern Med 163: 427-436
7. Yki-Jarvinen H 2005 Fat in the liver and insulin resistance. Ann Med 37:347-356
8. Matsuzawa Y: The role of fat topology in the risk of disease. Int J Obes (Lond) 2008, 32(Suppl 7):S83-S92.
9. Matsuzawa Y: Adiponectin: a key player in obesity related disorders. Curr Pharm Des 2010, 16:1896-1901.
10. Okamoto Y, Kihara S, Funahashi T, Matsuzawa Y, Libby P: Adiponectin: a key adipocytokine in metabolic syndrome. Clin Sci (Lond) 2006, 110:267-278.
11. Leung A. Encyclopedia of Common Natural Ingredients Used in Food, Drugs, and Cosmetics. New York, N.Y.: John Wiley; 1980:313-314.
12. Funk J L, Frye J B, Oyarzo J N, Zhang H, Timmermann B N. Anti-Arthritic Effects and Toxicity of the Essential Oils of Turmeric (*Curcuma longa* L.). Journal of Agricultural and Food Chemistry 2009; 58: 842-849.
13. Phan T T, See P, Lee S T, Chan S Y. Protective Effects of Curcumin against Oxidative Damage on Skin Cells In Vitro: Its Implication for Wound Healing. The Journal of Trauma: Injury, Infection, and Critical Care 2001; 51: 927-931.
14. Bhattacharya A, Chatterjee A, Ghosal S, Bhattacharya S K. Antioxidant activity of active tannoid principles of *Emblica officinalis* (Amla). Indian Journal of Experimental Biology 1999; 37:676☐680.
15. Jeena K J, Joy K L, Kuttan R Effect of *Phyllanthus emblica, Phyllanthus amarus* and *Picrorhiza kurroa* on N-Nitrosodiethylamine induced hepatocarcinogenesis. Cancer Letters 1999; 136: 11-16.
16. Mishra M, Pathak U N, Khan A B. *Emblica officinalis* Gaertn and serum cholesterol level in experimental rabbits. British Journal of Experimental Pathology 1981; 62:526-528.
17. Asmawi M Z, Kankaanranta H, Moilanen E, Vapaataslo H. Antiinflammatory activities of *Emblica officinalis* Gaertn leaf extracts. Journal of Pharmacy and Pharmacology 1993; 45:5811☐/584.
18. Rao, U. M., Sreenivasulu, M., Chengaiah, B., Reddy, K. J., Chetty, C. M., 2010. Herbal medicines for diabetes mellitus: a review. International Journal of PharmTech Research 2, 1883-1892
19. Stanely M, Prince P, Menon V P. Antioxidant action of *Tinospora cordifolia* root extract in alloxan diabetic rats. Phytother Res 2001; 15:213-8.
20. Prince P S, Menon V P. Antioxidant activity of *Tinospora cordifolia* roots in experimental diabetes. J Ethnopharmacol 1999; 65:277-81.
21. Mathew S, Kuttan G. Antioxidant activity of *Tinospora cordifolia* and its usefulness in the amelioration of cyclophosphamide-induced toxicity. J Exp Clin Cancer Res 1997; 16:407-11
22. Ajabnoor M A, Tilmisany A K. Effect of *Trigonella foenum graecum* on blood glucose levels in normal and alloxan-diabetic mice. J Ethnopharmacol 1988; 22:45-49.
23. Amin R, Abdul-Ghani A S, Suleiman M S. Effect of *Trigonella foenum graecum* on intestinal absorption.

Proc. of the 47th Annual Meeting of the American Diabetes Association (Indianapolis U.S.A.). Diabetes 1987; 36:211a.
24. Firoz N Momin, Bharatesh R Kalai, Tabassum S Shikalgar, Nilofar S Naikwade. Cardioprotective effect of methanolic extract of Ixora coccinea Linn. leaves on doxorubicin-induced cardiac toxicity in rats. Indian Journal of Pharmacology. 2012; 44 (2): 178-183
25. Yasmeen Maniyarl, Prabhu Bhixavatimathl, N V Agashikar. Antidiarrheal activity of flowers of Ixora Coccinea Linn. in rats. Journal of Ayurvedic and Integrated Medicine. 2010. 1 (4): 287-291
26. H. Sagrawat, A. Mann and M. Kharya, "Pharmacological Potential of Eugenia Jambolana: A Review," Pharmacogenesis Magazice, Vol. 2, 2006, pp. 96-104.

We claim:

1. A method for treating metabolic syndrome, comprising administering an effective amount of an herbal composition to a subject in need thereof, wherein the herbal composition is obtained by:
   (a) preparing a first herb blend by selecting at least four herbs selected from the group consisting of Curcuma longa, Emblica officinalis, Vernonia anthelmintica, Tinospora cordifoha, Trigonella foenum-graecum, Ixora coccinea, Syzygium cumini, wherein the first herbs selected in the first herb blend are present in equal amounts by weight;
   (b) extracting the first herb blend by a hydro-alcohol extraction process to obtain a first herb blend extract solution;
   (c) preparing a second herb blend comprising herbs Curcuma longa and Emblica officinalis in a ratio of 1:1 to 1:3;
   (d) extracting the second herb blend by the hydro-alcohol extraction process to obtain a second herb blend extract solution; and
   (e) mixing the first herb blend extract solution and the second herb blend extract solution in a ratio of 1:1 to obtain an extract mix;
   distilling and concentrating the extract mix to obtain the herbal composition; and
   formulating the herbal composition in a suitable dosage form including powder or paste, wherein the hydro-alcohol extraction process comprises:
   pulverizing and sifting the herbs;
   obtaining an extract using a solvent that includes a mixture of alcohol and water in a ratio within a range of 80:20 to 20:80, at reflux or under circulation at 75° C. for 2 hours; and
   filtering the extract to obtain the herb blend extract solution.

2. The method of claim 1, wherein:
   the first herb blend comprises herbs Curcuma longa, Emblica officinalis, Vernonia anthelmintica, Tinospora cordifolia, Trigonella foenum-graecum, Ixora coccinea and Syzygium curnini wherein the said herbs are present in equal amounts.

3. The method of claim 1, wherein:
   the first herb blend optionally comprises herbs Curcuma longa, Emblica officinalis, Vernonia anthelmintica, Tinospora cordifolia, Trigonella foenum-graecum and Ixora coccinea wherein the said herbs are present in equal amounts.

4. The method of claim 1, wherein:
   the first herb blend optionally comprises herbs Curcuma longa, Emblica officinalis, Vernonia anthelmintica, Tinospora cordifolia and Trigonella foenum-graecum wherein the said herbs are present in equal amounts.

5. The method of claim 1, wherein:
   the first herb blend optionally, comprises herbs from Curcuma longa, Emblica officinalis, Vernonia anthelmintica and Tinospora cordifolia wherein the said herbs are present in equal amounts.

6. The method of claim 1, wherein the herbal composition further comprises pharmaceutically acceptable excipients, wherein the excipients are selected from a group consisting of additives, gums, sweeteners, coatings, binders, disintegrants, lubricants, disintegration agents, suspending agents, granulating agents, solvents, colorants, glidants, anti-adherents, anti-static agents, surfactants, plasticizers, emulsifying agents, flavoring agents, viscosity enhancers and antioxidants to provide a pharmaceutical composition.

7. The method of claim 1, wherein the herbal composition is formulated to prepare suitable dosage forms selected from a group consisting of granule, capsule, tablet, liquid, lozenges, beverages, emulsion, suspension, syrups, elixirs, oral drops, jellies, phytoceuticals, food supplements and nutraceuticals.

8. The method of claim 7, wherein the herbal composition is used in wheat flour, soups, cookies, biscuits, dairy foods and other processed foods.

9. The method of claim 1, wherein the herbal composition is effective in management of disorders related to metabolic syndrome such as Type 2 diabetes by controlling blood glucose, in obesity, in lipid profile management of an individual in arresting body weight gain and in preventing body weight gain on a continued therapy basis.

10. The method of claim 1, wherein the first herb blend optionally, comprises herbs Tinospora cordifolia, Trigonella foenum-graecum, Ixora coccinea, Syzygium cumini wherein the said herbs are present in equal amounts; and the second herb blend comprises herbs Curcuma longa and Emblica officinalis in a ratio of 1:1 to 1:3.

11. The method of claim 10, wherein an effective amount of the herbal composition is administered to a patient to reduce glucose in plasma, reduce triglyceride levels in plasma, and to reduce serum cholesterol levels.

12. The method of claim 1, wherein the specific plant parts of raw herbs in the first herb blend and the second herb blend comprise dried rhizome of Curcuma longa, stem of Tinospora cordifolia, dried pericarp of Emblica officinalis, root of Ixora coccinea, bark of Syzygium cumini, seeds of Trigonella foenum-graecum and fruits of Vernonia anthelmintica.

13. The method of claim 1, wherein the alcohol in the solvent is selected from methyl alcohol, ethyl alcohol and iso-propyl alcohol, preferably ethyl alcohol.

14. The method of claim 13, wherein the ratio of alcohol and water in the solvent is 50:50 or 70:30.

15. The method of claim 1, wherein an effective amount of the herbal composition is administered to a patient to reduce glucose in plasma, reduce triglyceride levels in plasma, and to reduce serum cholesterol levels.

16. The method of claim 1, wherein the herbal composition is used in preparation of food products and beverages, including tea, infusions, drinks, and water.

* * * * *